(12) United States Patent
Wakasugi et al.

(10) Patent No.: US 12,267,476 B2
(45) Date of Patent: Apr. 1, 2025

(54) PROPERTY DISPLAY DEVICE, PROPERTY DISPLAY METHOD, AND NON-TRANSITORY COMPUTER-READABLE MEDIUM

(71) Applicant: Panasonic Intellectual Property Management Co., Ltd., Osaka (JP)

(72) Inventors: Kensuke Wakasugi, Tokyo (JP); Takehiro Tanaka, Hyogo (JP); Koji Morikawa, Tokyo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 1 day.

(21) Appl. No.: 17/938,530

(22) Filed: Oct. 6, 2022

(65) Prior Publication Data
US 2023/0034028 A1 Feb. 2, 2023

Related U.S. Application Data

(63) Continuation of application No. PCT/JP2021/016565, filed on Apr. 26, 2021.

(30) Foreign Application Priority Data

Apr. 30, 2020 (JP) ................. 2020-080020

(51) Int. Cl.
*H04N 1/60* (2006.01)
*G06F 16/28* (2019.01)

(52) U.S. Cl.
CPC ......... *H04N 1/6055* (2013.01); *G06F 16/283* (2019.01)

(58) Field of Classification Search
CPC ..... H04N 1/6055; G06F 16/283; G06F 30/12; G16C 20/80
See application file for complete search history.

(56) References Cited

U.S. PATENT DOCUMENTS

| | | | | |
|---|---|---|---|---|
| 6,134,537 A | * | 10/2000 | Pao | ............ G06F 18/21355 706/26 |
| 7,199,809 B1 | * | 4/2007 | Lacy | .............. G16C 20/60 702/19 |

(Continued)

FOREIGN PATENT DOCUMENTS

JP        2004-086892        3/2004

OTHER PUBLICATIONS

Extended European Search Report issued Sep. 25, 2023 in corresponding European Patent Application No. 21797815.4.

(Continued)

*Primary Examiner* — Ann J Lo
*Assistant Examiner* — Fernando M Mari Valcarcel
(74) *Attorney, Agent, or Firm* — Wenderoth, Lind & Ponack, L.L.P.

(57) ABSTRACT

A property display device includes: a search content acquirer that acquires search variables and search data; a property value acquirer that acquires property values of a compound corresponding to the search data; a priority setter that sets a priority of the search variables; a display format determiner that determines a display format of the property of the compound by assigning search variables of high priority to coordinate axes A1 and A2 of color maps Ma and assigning search variables of lower priority than the search variables of high priority to array direction axes A3 and A4 of a first array map Mb1; and an image processor that generates at least one first array map Mb1 as a single image on the basis of the search data, the property values, and the display format.

3 Claims, 30 Drawing Sheets

(56) References Cited

U.S. PATENT DOCUMENTS

| | | | |
|---|---|---|---|
| 9,710,953 B2* | 7/2017 | Fukazawa | G06T 11/206 |
| 10,372,713 B1* | 8/2019 | Blake | G16C 20/70 |
| 2010/0070339 A1* | 3/2010 | Bae | G06Q 30/02 |
| | | | 705/7.11 |
| 2016/0240682 A1 | 8/2016 | Shimomura et al. | |
| 2017/0308825 A1* | 10/2017 | Motohashi | G06Q 10/063 |
| 2019/0316209 A1* | 10/2019 | Hubbell | C12Q 1/6806 |
| 2020/0097869 A1* | 3/2020 | Bajaj | G06Q 10/0635 |
| 2020/0105033 A1* | 4/2020 | Chopra | G06T 11/206 |

OTHER PUBLICATIONS

Thompson, Travis et al., "Electrochemical Window of the Li-Ion Solid Electrolyte $Li_7La_3Zr_2O_{12}$", ACS Energy Letters, vol. 2, No. 2, Jan. 27 2017 (Jan. 27, 2017), pp. 462-468, XP093081981.

International Search Report of PCT application No. PCT/JP2021/016565 dated Jul. 20, 2021.

Jonathan Schmidt et al., "Predicting the Thermodynamic Stability of Solids Combining Density Functional Theory and Machine Learning" Chemistry of Materials, 29(12), 2017, May 15, 2017, pp. 5090-5103.

Austin D. Sendek et al., "Holistic computational structure screening of more than 12000 candidates for solid lithium-ion conductor materials" Energy & Environmental Science, 10(1), 2017, Dec. 1, 2016, pp. 306-320.

Xingfeng He et al., "Statistical variances of diffusional properties from ab initio molecular dynamics simulations" npj Computational Materials, 4(1), 2018, Apr. 3, 2018, pp. 1-9.

\* cited by examiner

FIG. 2

SEARCH CONTENT     COMPOUND: $Li_{2-3a-4b}(M3_{1-x}M3'_x)_a(M4_{1-y}M4'_y)_{1+b}O_3$

| CATEGORY VARIABLES | SEARCH VARIABLE | SEARCH DATA | NUMBER OF SEARCH DATA POINTS (NUMBER OF COMBINATIONS) |
|---|---|---|---|
| | M3, M3' | La, Al, Ga, In | 6 |
| | M4, M4' | Ti, Zr, Hf | 3 |

| DISCRETE VARIABLES | SEARCH VARIABLE | SEARCH DATA | NUMBER OF SEARCH DATA POINTS |
|---|---|---|---|
| | a | 0.0, 0.05, 0.1, 0.15, 0.2 | 5 |
| | b | 0.0, 0.1, 0.2, 0.3 | 4 |

| CONTINUOUS VARIABLES | SEARCH VARIABLE | SEARCH DATA | | | NUMBER OF SEARCH DATA POINTS |
|---|---|---|---|---|---|
| | | MINIMUM VALUE | MAXIMUM VALUE | STEP SIZE | |
| | x | 0.0 | 1.0 | 0.1 | 11 |
| | y | 0.0 | 1.0 | 0.1 | 11 |

FIG. 3

| SEARCH CONTENT | | SEARCH VARIABLE | SEARCH DATA | NUMBER OF SEARCH DATA POINTS (NUMBER OF COMBINATIONS) |
|---|---|---|---|---|
| CATEGORY VARIABLES | | M3, M3' | La, Al, Ga, In | 6 |
| | | M4, M4' | Ti, Zr, Hf | 3 |
| | | SINTERING METHOD | SOLID-PHASE REACTION METHOD, BALL MILL | 2 |

| | SEARCH VARIABLE | SEARCH DATA | NUMBER OF SEARCH DATA POINTS |
|---|---|---|---|
| DISCRETE VARIABLES | a | 0.0, 0.05, 0.1, 0.15, 0.2 | 5 |
| | b | 0.0, 0.1, 0.2, 0.3 | 4 |
| | SINTERING TIME (h) | 1, 2, 3 | 3 |

| | SEARCH VARIABLE | SEARCH DATA | NUMBER OF SEARCH DATA POINTS |
|---|---|---|---|
| CONTINUOUS VARIABLES | x | 0.0, 0.1, 0.2, 0.3, 0.4, 0.5, 0.6, 0.7, 0.8, 0.9, 1.0 | 11 |
| | y | 0.0, 0.1, 0.2, 0.3, 0.4, 0.5, 0.6, 0.7, 0.8, 0.9, 1.0 | 11 |
| | SINTERING TEMPERATURE (°C) | 100, 110, 120, 130, 140, 150, 160 | 7 |

FIG. 4

| COMBINED SEARCH DATA | SEARCH VARIABLES AND SEARCH DATA | | | | | | | |
|---|---|---|---|---|---|---|---|---|
| | M3 | M3' | M4 | M4' | a | b | x | y |
| Li1.45La0.05Ti1.1O3 | La | Al | Ti | Zr | 0.05 | 0.1 | 0 | 0 |
| Li1.45La0.05Zr0.11Ti0.99O3 | La | Al | Ti | Zr | 0.05 | 0.1 | 0 | 0.1 |
| Li1.45La0.05Zr0.22Ti0.88O3 | La | Al | Ti | Zr | 0.05 | 0.1 | 0 | 0.2 |
| Li1.45La0.05Zr0.33Ti0.77O3 | La | Al | Ti | Zr | 0.05 | 0.1 | 0 | 0.3 |
| Li1.45La0.05Zr0.44Ti0.66O3 | La | Al | Ti | Zr | 0.05 | 0.1 | 0 | 0.4 |
| Li1.45La0.05Zr0.55Ti0.55O3 | La | Al | Ti | Zr | 0.05 | 0.1 | 0 | 0.5 |
| Li1.45La0.05Zr0.66Ti0.44O3 | La | Al | Ti | Zr | 0.05 | 0.1 | 0 | 0.6 |
| Li1.45La0.05Zr0.77Ti0.33O3 | La | Al | Ti | Zr | 0.05 | 0.1 | 0 | 0.7 |
| Li1.45La0.05Zr0.88Ti0.22O3 | La | Al | Ti | Zr | 0.05 | 0.1 | 0 | 0.8 |
| Li1.45La0.05Zr0.99Ti0.11O3 | La | Al | Ti | Zr | 0.05 | 0.1 | 0 | 0.9 |
| Li1.45La0.05Zr1.1O3 | La | Al | Ti | Zr | 0.05 | 0.1 | 0 | 1 |
| Li1.45La0.045Zr0.11Ti1.1Al0.005O3 | La | Al | Ti | Zr | 0.05 | 0.1 | 0.1 | 0 |
| Li1.45La0.045Zr0.11Ti0.99Al0.005O3 | La | Al | Ti | Zr | 0.05 | 0.1 | 0.1 | 0.1 |
| Li1.45La0.045Zr0.22Ti0.88Al0.005O3 | La | Al | Ti | Zr | 0.05 | 0.1 | 0.1 | 0.2 |
| Li1.45La0.045Zr0.33Ti0.77Al0.005O3 | La | Al | Ti | Zr | 0.05 | 0.1 | 0.1 | 0.3 |
| Li1.45La0.045Zr0.44Ti0.66Al0.005O3 | La | Al | Ti | Zr | 0.05 | 0.1 | 0.1 | 0.4 |
| Li1.45La0.045Zr0.55Ti0.55Al0.005O3 | La | Al | Ti | Zr | 0.05 | 0.1 | 0.1 | 0.5 |
| Li1.45La0.045Zr0.66Ti0.44Al0.005O3 | La | Al | Ti | Zr | 0.05 | 0.1 | 0.1 | 0.6 |
| Li1.45La0.045Zr0.77Ti0.33Al0.005O3 | La | Al | Ti | Zr | 0.05 | 0.1 | 0.1 | 0.7 |
| Li1.45La0.045Zr0.88Ti0.22Al0.005O3 | La | Al | Ti | Zr | 0.05 | 0.1 | 0.1 | 0.8 |
| Li1.45La0.045Zr0.99Ti0.11Al0.005O3 | La | Al | Ti | Zr | 0.05 | 0.1 | 0.1 | 0.9 |
| Li1.45La0.045Zr1.1Al0.005O3 | La | Al | Ti | Zr | 0.05 | 0.1 | 0.1 | 1 |

FIG. 5

| COMBINED SEARCH DATA | SEARCH VARIABLES AND SEARCH DATA | | | | | | | PROPERTY VALUE |
|---|---|---|---|---|---|---|---|---|
| | M3 | M3' | M4 | M4' | a | b | x | y | |
| Li1.45La0.05Ti1.1O3 | La | Al | Ti | Zr | 0.05 | 0.1 | 0 | 0 | 2.350 |
| Li1.45La0.05Zr0.11Ti0.99O3 | La | Al | Ti | Zr | 0.05 | 0.1 | 0 | 0.1 | 2.366 |
| Li1.45La0.05Zr0.22Ti0.88O3 | La | Al | Ti | Zr | 0.05 | 0.1 | 0 | 0.2 | 2.437 |
| Li1.45La0.05Zr0.33Ti0.77O3 | La | Al | Ti | Zr | 0.05 | 0.1 | 0 | 0.3 | 2.565 |
| Li1.45La0.05Zr0.44Ti0.66O3 | La | Al | Ti | Zr | 0.05 | 0.1 | 0 | 0.4 | 2.599 |
| Li1.45La0.05Zr0.55Ti0.55O3 | La | Al | Ti | Zr | 0.05 | 0.1 | 0 | 0.5 | 2.573 |
| Li1.45La0.05Zr0.66Ti0.44O3 | La | Al | Ti | Zr | 0.05 | 0.1 | 0 | 0.6 | 2.561 |
| Li1.45La0.05Zr0.77Ti0.33O3 | La | Al | Ti | Zr | 0.05 | 0.1 | 0 | 0.7 | 2.622 |
| Li1.45La0.05Zr0.88Ti0.22O3 | La | Al | Ti | Zr | 0.05 | 0.1 | 0 | 0.8 | 2.586 |
| Li1.45La0.05Zr0.99Ti0.11O3 | La | Al | Ti | Zr | 0.05 | 0.1 | 0 | 0.9 | 2.639 |
| Li1.45La0.05Zr1.1O3 | La | Al | Ti | Zr | 0.05 | 0.1 | 0 | 1 | 2.619 |
| Li1.45La0.045Ti1.1Al0.005O3 | La | Al | Ti | Zr | 0.05 | 0.1 | 0.1 | 0 | 2.349 |
| Li1.45La0.045Zr0.11Ti0.99Al0.005O3 | La | Al | Ti | Zr | 0.05 | 0.1 | 0.1 | 0.1 | 2.371 |
| Li1.45La0.045Zr0.22Ti0.88Al0.005O3 | La | Al | Ti | Zr | 0.05 | 0.1 | 0.1 | 0.2 | 2.462 |
| Li1.45La0.045Zr0.33Ti0.77Al0.005O3 | La | Al | Ti | Zr | 0.05 | 0.1 | 0.1 | 0.3 | 2.558 |
| Li1.45La0.045Zr0.44Ti0.66Al0.005O3 | La | Al | Ti | Zr | 0.05 | 0.1 | 0.1 | 0.4 | 2.607 |
| Li1.45La0.045Zr0.55Ti0.55Al0.005O3 | La | Al | Ti | Zr | 0.05 | 0.1 | 0.1 | 0.5 | 2.578 |
| Li1.45La0.045Zr0.66Ti0.44Al0.005O3 | La | Al | Ti | Zr | 0.05 | 0.1 | 0.1 | 0.6 | 2.559 |
| Li1.45La0.045Zr0.77Ti0.33Al0.005O3 | La | Al | Ti | Zr | 0.05 | 0.1 | 0.1 | 0.7 | 2.612 |
| Li1.45La0.045Zr0.88Ti0.22Al0.005O3 | La | Al | Ti | Zr | 0.05 | 0.1 | 0.1 | 0.8 | 2.572 |
| Li1.45La0.045Zr0.99Ti0.11Al0.005O3 | La | Al | Ti | Zr | 0.05 | 0.1 | 0.1 | 0.9 | 2.621 |
| Li1.45La0.045Zr1.1Al0.005O3 | La | Al | Ti | Zr | 0.05 | 0.1 | 0.1 | 1 | 2.594 |

FIG. 6

| | CATEGORY VARIABLES | | DISCRETE VARIABLES | | CONTINUOUS VARIABLES | |
|---|---|---|---|---|---|---|
| | A SMALL NUMBER OF SEARCH DATA POINTS | A LARGE NUMBER OF SEARCH DATA POINTS | A SMALL NUMBER OF SEARCH DATA POINTS | A LARGE NUMBER OF SEARCH DATA POINTS | A SMALL NUMBER OF SEARCH DATA POINTS | MINIMUM 0, MAXIMUM 1 AND NUMBER OF SEARCH DATA POINTS ≥ 5 |
| | | | | | A LARGE NUMBER OF SEARCH DATA POINTS | |
| | M4, M4' | M3, M3' | b | a | — | y, x |

LOW ←——— PRIORITY ———→ HIGH

FIG. 8

| | SEARCH VARIABLES AND ASSIGNED AXES | | |
|---|---|---|---|
| COORDINATE AXIS A1 | COORDINATE AXIS A2 | ARRAY DIRECTION AXIS A3 | ARRAY DIRECTION AXIS A4 |
| x | y | a | b |

| OTHER SEARCH VARIABLES NOT ASSIGNED TO COORDINATE AXES OR ARRAY DIRECTION AXES |
|---|
| M3, M3', M4, M4' |

FIG. 13

COMPOUND: $Li_{2-3a-4b}(Al_{1-x}Ga_x)_a(Ti_{1-y}Zr_y)_{1+b}O$

| SEARCH CONTENT | | |
|---|---|---|
| VARIABLE | SEARCH DATA | NUMBER OF SEARCH DATA POINTS |
| a | 0.0, 0.05, 0.1, 0.15, 0.2 | 5 |
| b | 0.0, 0.1, 0.2, 0.3 | 4 |
| x | 0.0, 0.1, 0.2, 0.3, 0.4, 0.5, 0.6, 0.7, 0.8, 0.9, 1.0 | 11 |
| y | 0.0, 0.1, 0.2, 0.3, 0.4, 0.5, 0.6, 0.7, 0.8, 0.9, 1.0 | 11 |

FIG. 17

COMPOUND: $M1(M2_{1-x-y}M2'_xM2''_y)$

SEARCH CONTENT

| CATEGORY VARIABLES | SEARCH VARIABLE | SEARCH DATA | NUMBER OF SEARCH DATA POINTS (NUMBER OF COMBINATIONS) |
|---|---|---|---|
| | M1 | Se, O, As, N | 4 |
| | M2, M2', M2'' | Si, Ge, Zn, Cd, In | 10 |

| CONTINUOUS VARIABLES | SEARCH VARIABLE | SEARCH DATA | | | NUMBER OF SEARCH DATA POINTS |
|---|---|---|---|---|---|
| | | MINIMUM VALUE | MAXIMUM VALUE | STEP SIZE | |
| | x | 0.0 | 1.0 | 0.1 | 11 |
| | y | 0.0 | 1.0 | 0.1 | 11 |

WHERE $x+y \leq 1$

PROPERTY DISPLAY DEVICE, PROPERTY DISPLAY METHOD, AND NON-TRANSITORY COMPUTER-READABLE MEDIUM

BACKGROUND

1. Technical Field

The present disclosure relates to a property display device and a property display method for displaying a property of a compound, and to a non-transitory computer-readable medium storing a program for executing the property display method.

2. Description of the Related Art

In materials development of the related art, to search for a composition formula or the process conditions of a compound having a desired property, experiments are performed while changing the proportional ratios of the raw materials and the like, and the composition formula or process conditions having a favorable property are specified. To display the differences in the property when factors such as the composition formula or the process conditions of the compound are changed, the methods indicated below has been disclosed, for example.

Japanese Patent No. 6632412 discloses a method for displaying material properties on a ternary plot when the organization of a composition formula is changed. U.S. Pat. No. 7,199,809 discloses a method for displaying properties by arranging, in a matrix form, data illustrated by a pie chart. Japanese Patent No. 4009670 discloses a method in which proportional ratios of a huge number of raw materials are inputted, and proportional ratios having a targeted property are outputted.

Moreover, recently, technologies for predicting the material properties of any composition formula by using a predictor obtained through machine learning are being developed. For example, a method for predicting the thermodynamic stability of perovskite materials by using a neural network is disclosed in Jonathan Schmidt et al., "Predicting the Thermodynamic Stability of Solids Combining Density Functional Theory and Machine Learning", Chemistry of Materials, 29(12), 5090-5103 (2017).

Also, a method for predicting a probability value that a compound exhibits high ionic conductivity is disclosed in Austin D. Sendek et al., "Holistic computational structure screening of more than 12000 candidates for solid lithium-ion conductor materials", Energy & Environmental Science, 10(1), 306-320 (2017). A method for calculating ion diffusion coefficients is disclosed in Xingfeng He et al., "Statistical variances of diffusional properties from ab initio molecular dynamics simulations", npj Computational Materials, 4(1), 1-9 (2018).

SUMMARY

However, in the technologies of the related art cited above, there are few types of search variables for searching for a composition formula or process conditions of a compound or the display method is a method for displaying localized data, and therefore it is difficult to recognize an overall picture of a property of the compound when the composition of the compound is changed.

One non-limiting and exemplary embodiment provides a property display device, a property display method, and a non-transitory computer-readable medium that make it possible to recognize an overall picture of a property of a compound when the composition of the compound is changed.

In one general aspect, the techniques disclosed here feature a property display device including: a search content acquirer that acquires search variables that determine the composition of a compound when searching for a property of the compound by changing the composition of the compound and search data indicating the values or ranges that the search variables take; a property value acquirer that acquires property values of the compound corresponding to the search data; a priority setter that sets a priority of the search variables; a display format determiner that determines the display format of the property of the compound by assigning search variables of high priority from among the search variables to the coordinate axes of color maps indicating the property of the compound and assigning search variables of lower priority than the search variables of high priority to the array direction axes of a first array map in which the color maps are arranged; and an image processor that generates at least one first array map as a single image on the basis of the search data, the property values, and the display format.

It should be noted that general or specific embodiments may be implemented as a device, a system, a method, an integrated circuit, a computer program, a non-transitory computer-readable recording medium, or any selective combination thereof. The computer-readable recording medium includes a non-volatile recording medium such as Compact Disc-Read-Only Memory (CD-ROM), for example.

According to the property display device and the like of the present disclosure, it is possible to recognize an overall picture of a property of a compound when the composition of the compound is changed. Additional benefits and advantages according to an aspect of the present disclosure will become apparent from the specification and the drawings. The benefits and/or advantages may be individually obtained by the various embodiments and features of the specification and drawings, which need not all be provided in order to obtain one or more of such benefits and/or advantages.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 2 is a diagram illustrating an example of compound search content inputted into the property display device of Embodiment 1;

FIG. 3 is a diagram illustrating another example of compound search content inputted into the property display device of Embodiment 1;

FIG. 4 is a table illustrating an example of combined search data generated on the basis of search content;

FIG. 5 is a table illustrating an example of combined search data and property values;

FIG. 6 is a diagram illustrating an example of a priority set with respect to search variables included in search content;

FIG. 8 is a diagram illustrating an example of assigning search variables to the coordinate axes of the color maps and the array direction axes of the first array map;

FIG. 13 is a diagram illustrating an example of search content inputted into a property display device according to Modification 1 of Embodiment 1;

FIG. 17 is a diagram illustrating an example of search content inputted into a property display device according to Modification 3 of Embodiment 1;

Figure 1:
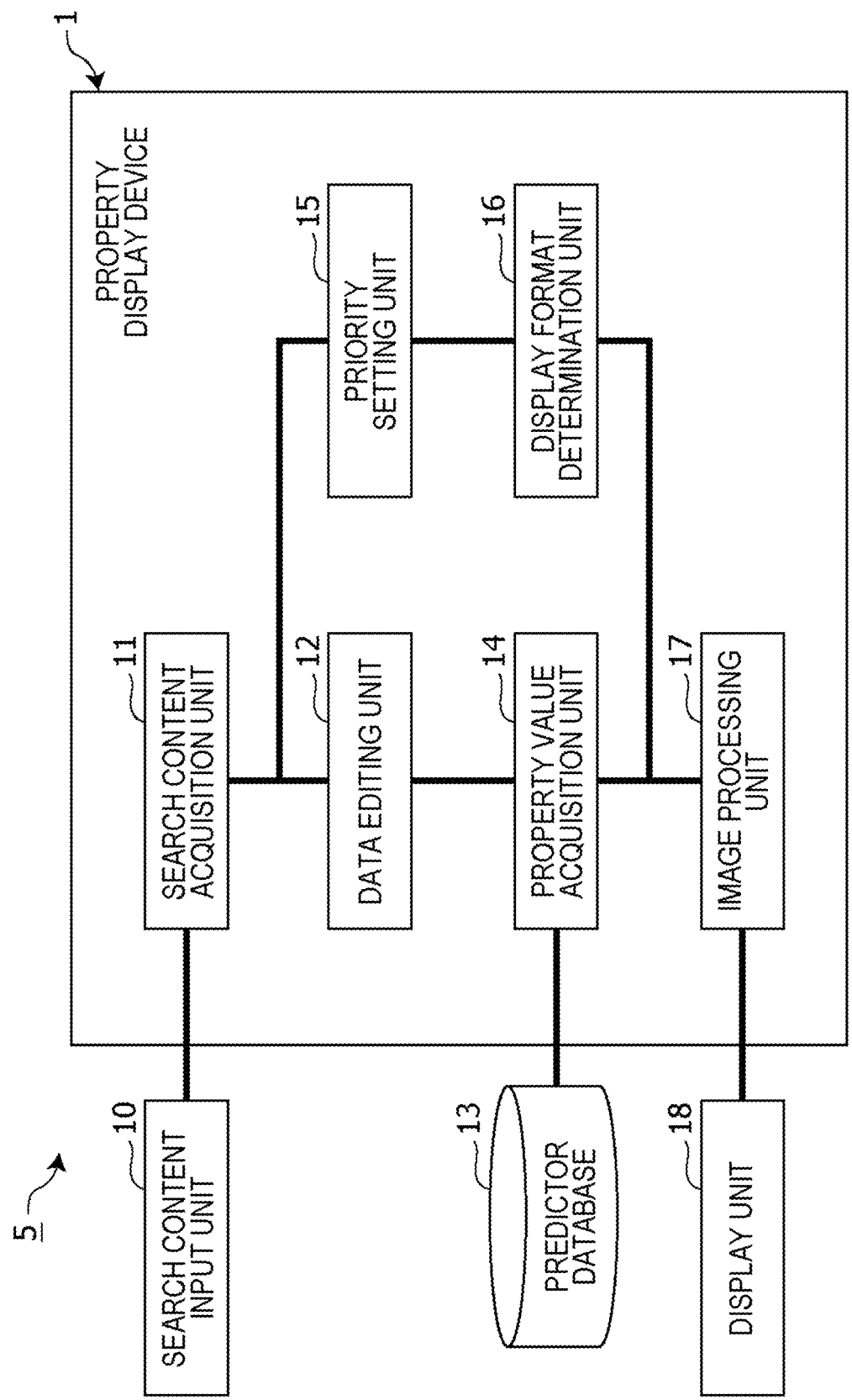
FIG. 1 is a block diagram illustrating a functional configuration of a property display system provided with a property display device according to Embodiment 1.

DETAILED DESCRIPTION (Underlying Knowledge Forming Basis of the Present Disclosure)

Recently, in fields such as image recognition and natural language processing, significant advances have been made in recognition and identification methods using machine learning and the like, and these methods are also beginning to be applied to the prediction of material properties.

For example, Schmidt et al. disclose a method for predicting the thermodynamic stability of perovskite materials by using a neural network. Perovskite materials are expressed by the composition formula $ABX\_3$, in which different elements are assigned to A, B, and X. According to the method disclosed by Schmidt et al., it is possible to predict the thermodynamic stability of a composition formula in which an unexamined combination of elements is assigned to A, B, and X, or the thermodynamic stability of a composition formula in which two or more elements are assigned to A (or B, or X) such that the sum of the coefficients is 1. According to this method, the number of experiments involving man-hours can be decreased, and materials development can be promoted.

However, although the technology disclosed by Schmidt et al. is capable of outputting a huge number of prediction results, each of the prediction results is presented individually, making it difficult to recognize an overall picture of the prediction results.

Japanese Patent No. 6632412 discloses a method for displaying properties on a ternary plot when the organization of a composition formula is changed. However, the display of the ternary plot disclosed in Japanese Patent No. 6632412 is limited to the presentation of three-element proportional ratios, or in other words the range that is expressed by two search variables. For this reason, when there are many types of search variables for a compound, it is difficult to recognize an overall picture of a property of the compound.

U.S. Pat. No. 7,199,809 discloses a method for displaying properties by arranging, in a matrix form, data illustrated by a pie chart. However, in the technology disclosed in U.S. Pat. No. 7,199,809, in the case of a compound having many types of search variables, such as perovskite materials, for example, it is difficult to recognize an overall picture of a property of the compound.

Japanese Patent No. 4009670 discloses a method in which proportional ratios of a huge number of raw materials are inputted, and proportional ratios having a targeted property are outputted. However, in the technology disclosed in Japanese Patent No. 4009670, since the output result is presented in a localized way, it is difficult to recognize an overall picture of a property of a compound.

In contrast, the property display device and the like of the present disclosure displays a property of a compound by forming a single image containing color maps indicating the property of the compound and an array map in which the color maps are arranged, assigning search variables with a high priority to the coordinate axes of each color map, and assigning search variables with a low priority to the array direction axes of the array map. This configuration makes it possible to recognize an overall picture of a property of a compound when the composition of the compound is changed.

Hereinafter, embodiments of the present disclosure will be described with reference to the drawings. The embodiments described hereinafter all illustrate specific examples of the present disclosure. Consequently, features such as numerical values, shapes, materials, structural elements, and the layout positions and connection configurations of the structural elements indicated in the following embodiments are merely examples, and are not intended to limit the present disclosure. Therefore, among the structural elements in the following embodiments, structural elements that are not described in the independent claim indicating the broadest concept of the present disclosure are described as optional structural elements.

Note that each diagram is a schematic diagram, and does not necessarily illustrate a strict representation. Also, in the drawings, structural elements that are substantially the same are denoted with the same signs, and duplicate description of such structural elements will be omitted or simplified.

Embodiment 1

[1-1. Configuration of Property Display Device and Property Display System]

A property display device and property display system according to Embodiment 1 will be described with reference to FIGS. 1 to 11.

FIG. 1 is a block diagram illustrating a functional configuration of a property display system 5 provided with a property display device 1 according to Embodiment 1.

As illustrated in FIG. 1, the property display system 5 is provided with the property display device 1, a search content input unit 10, a predictor database 13, and a display unit 18. The property display device 1 is provided with a search content acquisition unit 11, a data editing unit 12, a property value acquisition unit 14, a priority setting unit 15, a display format determination unit 16, and an image processing unit 17.

The property display device 1 is configured by a processor such as a central processing unit (CPU), volatile memory and non-volatile memory, and a program stored in the non-volatile memory, for example. The functional configuration of the property display device 1 is achieved by executing the program.

The search content input unit 10 receives search content for a compound through input operations performed by a user, for example. Search content for a compound refers to the content of each composition of the compound for which a property of the compound is to be displayed when the composition of the compound is changed. Note that the search content may also include the designation of a specific compound from among multiple types of compounds. The search content input unit 10 may be a keyboard, a touch sensor, a touchpad, and/or a mouse, for example.

The present embodiment will be described by taking the example of a case in which the compound to be searched is a solid electrolyte and the composition formula of the compound is indicated by the following formula (1).

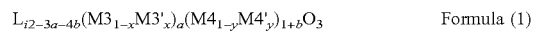

Formula (1)

Note that in formula (1), O is a composition not included in the current search content.

FIG. 2 is a diagram illustrating an example of search content inputted into the property display device 1. In FIG. 2, search variables and search data contained in the search content are illustrated.

The search variables are parameters determining the composition of the compound, and the search data is data indicating the values that the search variables may take or the ranges of the search variables. The search variables are category variables, discrete variables, and continuous variables, for example. The composition of a compound is not limited to the ratio of component elements, or in other words the composition ratio or the like, of the compound. The composition of a compound includes synthesis process conditions for synthesizing the compound, such as a sintering method, sintering time, and sintering temperature, for example. In other words, in formula (1), the composition formula of a compound is indicated as information using category variables, discrete variables, and continuous variables, but information about the compound is not limited to the variables included in the composition formula indicating the compound. The composition of a compound may also include synthesis process conditions for synthesizing the compound, such as parameters expressing a sintering method, sintering time, and sintering temperature, for example.

Category variables are types of elements composing a compound, for example. In formula (1), the combination of M3 and M3' and the combination of M4 and M4' correspond to category variables. FIG. 2 illustrates an example in which two elements from among the four elements of La, Al, Ga, and In are selected as an example of the combination of M3 and M3'. The number of combinations of M3 and M3', or in other words the number of search data points, is 6. FIG. 2 also illustrates an example in which two elements from among the three elements of Ti, Zr, and Hf are selected as an example of the combination of M4 and M4'. The number of combinations of M4 and M4', or in other words the number of search data points, is 3. Note that Li is an element fixed in advance and does not correspond to a category variable in this example.

Continuous variables are numerical values for determining the composition ratio of a compound. Continuous variables have a large number of search data points compared to discrete variables and category variables, and are suited to cases where it is desirable to carry out in-depth analysis of changes in property values with respect to changes in the search data. Continuous variables are variables for which the search data has a maximum value of 1 and a minimum value of 0, for example. In addition, for continuous variables, the number of search data points may be 5 or more.

In formula (1), x and y each correspond to a continuous variable. For example, the ratios of M3 and M3' expressed by the continuous variable x have an inverse correlation whereby if one of the ratios is changed, the other ratio also changes. Also, the ratios of M4 and M4' expressed by the continuous variable y have an inverse correlation whereby if one of the ratios is changed, the other ratio also changes. The continuous variables x and y illustrated in FIG. 2 have a minimum value of 0.0, a maximum value of 1.0, and the number of search data points is 11. Each search data point of the continuous variables x and y may be expressed by listing all the data points, such as 0.0, 0.1, 0.2, . . . , 1.0, or may be expressed by indicating a data interval, such as a step size of 0.1. The step size of the continuous variables illustrated in FIG. 2 may also be smaller than 0.1 so that the search data changes in more continuous way. Examples of smaller step sizes include 0.01 and 0.001. The user may also assign each of the search variables x and y as a continuous variable. In this case, the user designates a minimum value and a maximum value for each of the search variables x and y, and a value pre-stored in the property display device 1 may be used as the step size for each of the search variables x and y.

Discrete variables are numerical values for determining the composition ratio of a compound. In the case of discrete variables, the search data exists discretely, and there is a small number of search data points compared to continuous variables. In formula (1), a and b each correspond to a discrete variable. The search data of the discrete variable a illustrated in FIG. 2 is expressed in a state in which all the data points are listed, such as 0.0, 0.05, 0.1, 0.15, 0.2. The search data of the discrete variable b is expressed in a state in which all the data points are listed, such as 0.0, 0.1, 0.2, 0.3.

The search content for a compound may include a formula specifying the compound to be searched, the search variables, and the search data corresponding to the search variables.

The user may also use a keyboard to input a formula (formula (1)) specifying the compound to be searched into the property display device 1.

The user may also use a keyboard, touch sensor, touchpad, and/or mouse or the like to input, into the property display device 1, search data corresponding to search variables displayed on a display.

The user may input (Ti, Zr), (Ti, Hf), (Zr, Hf), (Zr, Ti), (Hf, Ti), (Hf, Zr) into the property display device 1 as the search data corresponding to the search variable (M4, M4'), input 0.0, 0.05, 0.1, 0.15, 0.2 into the property display device 1 as the search data corresponding to the search variable a, input 0.0, 0.1, 0.2, 0.3 into the property display device 1 as the search data corresponding to the search variable b, input 0.0, 0.1, 0.2, ..., 1.0 into the property display device 1 as the search data corresponding to the search variable x, and input 0.0, 0.1, 0.2, ..., 1.0 into the property display device 1 as the search data corresponding to the search variable y.

The search content acquisition unit 11 may also receive the inputted search content for a compound.

FIG. 3 is a diagram illustrating another example of search content inputted into the property display device 1. The search content in FIG. 3 includes variable information related to the production method, such as a sintering method as a category variable, a sintering time as a discrete variable, and a sintering temperature as a continuous variable. The search variables are not limited to the composition ratio or the like of the compound, and may also include the method of producing the compound, such as the sintering method, sintering temperature, and sintering temperature.

The search content input unit 10 outputs the search content for a compound inputted into the property display system 5 to the search content acquisition unit 11.

The search content acquisition unit 11 acquires the search content outputted from the search content input unit 10. Thereafter, the search content acquisition unit 11 outputs the acquired search content to each of the data editing unit 12 and the priority setting unit 15.

The data editing unit 12 generates all combinations that the search data included in the search content may take. With this step, combined search data is generated.

FIG. 4 is a table illustrating an example of combined search data generated on the basis of search content. In FIG. 4, the combined search data is represented in a listed state with one data point per row. Note that the method of representing the combined search data may also be one in which the combined search data is indicated in an internal order for each variable, rather than being listed as in FIG. 4. For example, if the discrete variable a is expressed in the order 0.0, 0.05, 0.1, 0.15, 0.2 as the internal order of the variable, in the case where the discrete variable a is to be set to a=0.1, the discrete variable a may be specified by indicating that the order of the discrete variable a is 3.

The data editing unit 12 outputs the combined search data to the property value acquisition unit 14 described later.

The predictor database 13 stores predictors for predicting the composition formulas of multiple types of compounds and property values of the compounds. A predictor is a program based on a prescribed computational algorithm. The predictor database 13 is formed from a non-volatile memory, for example. Note that the predictor database 13 may be in any format insofar as property values related to each search data point can be outputted.

The property values outputted from the predictor database 13 may be the property values calculated using the predictors described by Schmidt et al. and Sendek et al., for example. Schmidt et al. disclose a method for predicting the thermodynamic stability of perovskite materials. Sendek et al. disclose a method for predicting a probability value that a compound exhibits high ionic conductivity.

Additionally, the property values outputted from the predictor database 13 may also be property values calculated according to density functional theory. To perform processing with density functional theory, it is necessary to designate a crystal structure, but for example, if the composition formula is the same, the crystal structure of a known compound may be adopted, whereas if the composition formula is different, a partial site may be replaced with different elements to create a tentative crystal structure which may be used in density functional theory calculations. Alternatively, one crystal structure of a compound may be verified experimentally, and the crystal structure may be adopted to execute density functional theory in a way similar to the above.

Moreover, the property values outputted from the predictor database 13 may also be property values calculated using a technique called ab initio molecular dynamics (AIMD) which is described by He et al., for example. He et al. disclose a method for calculating ion diffusion coefficients. Note that the property values are not limited to predicted values and may also be property values obtained experimentally. Examples of the property values include electrical conductivity values and thermal conductivity values.

The predictor database 13 outputs, to the property value acquisition unit 14, a predictor according to a request by the property value acquisition unit 14, or in other words, a predictor suited to predicting a property of the compound.

The property value acquisition unit 14 acquires the combined search data outputted from the data editing unit 12 and acquires the predictor from the predictor database 13. The property value acquisition unit 14 uses the predictor to calculate property values for the combined search data, and acquires the property values of the compound.

FIG. 5 is a table illustrating an example of combined search data and property values. On the right edge of FIG. 5, the property values of the compound with respect to the combined search data are illustrated. The property values of the present embodiment are predicted values calculated by the predictor.

The property value acquisition unit 14 outputs the combined search data and the calculated property values in association with each other to the image processing unit 17.

The priority setting unit 15 sets the priority of the search variables on the basis of the search content outputted from the search content acquisition unit 11. A high priority is set when there is a need to closely examine the change in property values with respect to a change in the search data. In other words, if a search variable p has a number of values pn, a search variable q has a number of values qn, and pn>qn, the priority of the search variable p is set higher than the priority of the search variable q.

FIG. 6 is a diagram illustrating an example of the priority set with respect to search variables included in search content. The following description assumes that the search content is the content illustrated in FIG. 2. In FIG. 6, the priority is set higher for variables farther on the right side of the diagram. For example, from among the continuous variables x and y, the discrete variables a and b, and the category variables (M3, M3') and (M4, M4'), the priority setting unit 15 sets the highest priority for the continuous variables x and y which have the greatest number of search data points. In addition, the priority setting unit 15 sets the priority of the discrete variables a and b higher than the priority of the category variables (M3, M3') and (M4, M4').

Also, if multiple continuous variables exist, the priority setting unit 15 sets the priority for the continuous variables such that the larger the number of search data points a continuous variable has, the higher the priority is set. Note that as an exception, the priority setting unit 15 sets the highest priority for continuous variables in which the search data has a minimum value of 0, a maximum value of 1, and the number of search data points is equal to or greater than 5. Also, if the number of search data points is the same, the priority setting unit 15 sets the priority to the same level. In the example illustrated in FIG. 2, the continuous variables x and y both have a minimum value of 0, a maximum value of 1, and a number of search data points equal to or greater than 5, and therefore the priority setting unit 15 sets the priority of both to the same high level. In the case where there are three or more continuous variables, the priority setting unit 15 likewise sets the priority on the basis of the number of search data points.

Also, if multiple discrete variables exist, the priority setting unit 15 sets the priority for the discrete variables such that the larger the number of search data points a discrete variable has, the higher the priority is set. Also, if the number of search data points is the same, the priority setting unit 15 sets the priority to the same level. In the example illustrated in FIG. 2, the number of search data points for the discrete variable a is 5 and the number of search data points for the discrete variable b is 4, and therefore the priority setting unit 15 sets the priority of the discrete variable a higher than the discrete variable b. In the case where there are three or more discrete variables, the priority setting unit 15 likewise sets the priority on the basis of the number of search data points.

Also, if multiple category variables exist, the priority setting unit 15 sets the priority for the category variables such that the larger the number of search data points a category variable has, the higher the priority is set. Also, if the number of search data points is the same, the priority setting unit 15 sets the priority to the same level. In the example illustrated in FIG. 2, M3 and M3' are a combination of two selected from among four elements, and therefore the number of search data points is 6, while M4 and M4' are a combination of two selected from among three elements, and therefore the number of search data points is 2. Consequently, the priority setting unit 15 sets the priority of M3 and M3' higher than M4 and M4'. In the case where there are three or more category variables, the priority setting unit 15 likewise sets the priority on the basis of the number of search data points.

The priority setting unit 15 outputs the result of setting the priority as above to the display format determination unit 16.

The display format determination unit 16 determines the display format of the property of the compound on the basis of the result of setting the priority outputted from the priority setting unit 15. The display format determination unit 16 determines the display format of the property of the compound by assigning the search variables of high priority from among the search variables to the coordinate axes A1 and A2 of color maps Ma and assigning the search variables of lower priority than the search variables of high priority to the array direction axes A3 and A4 of a first array map Mb1 (see FIG. 7). Hereinafter, the color maps Ma, the first array map Mb1, and the like will be described.

Figure 7:
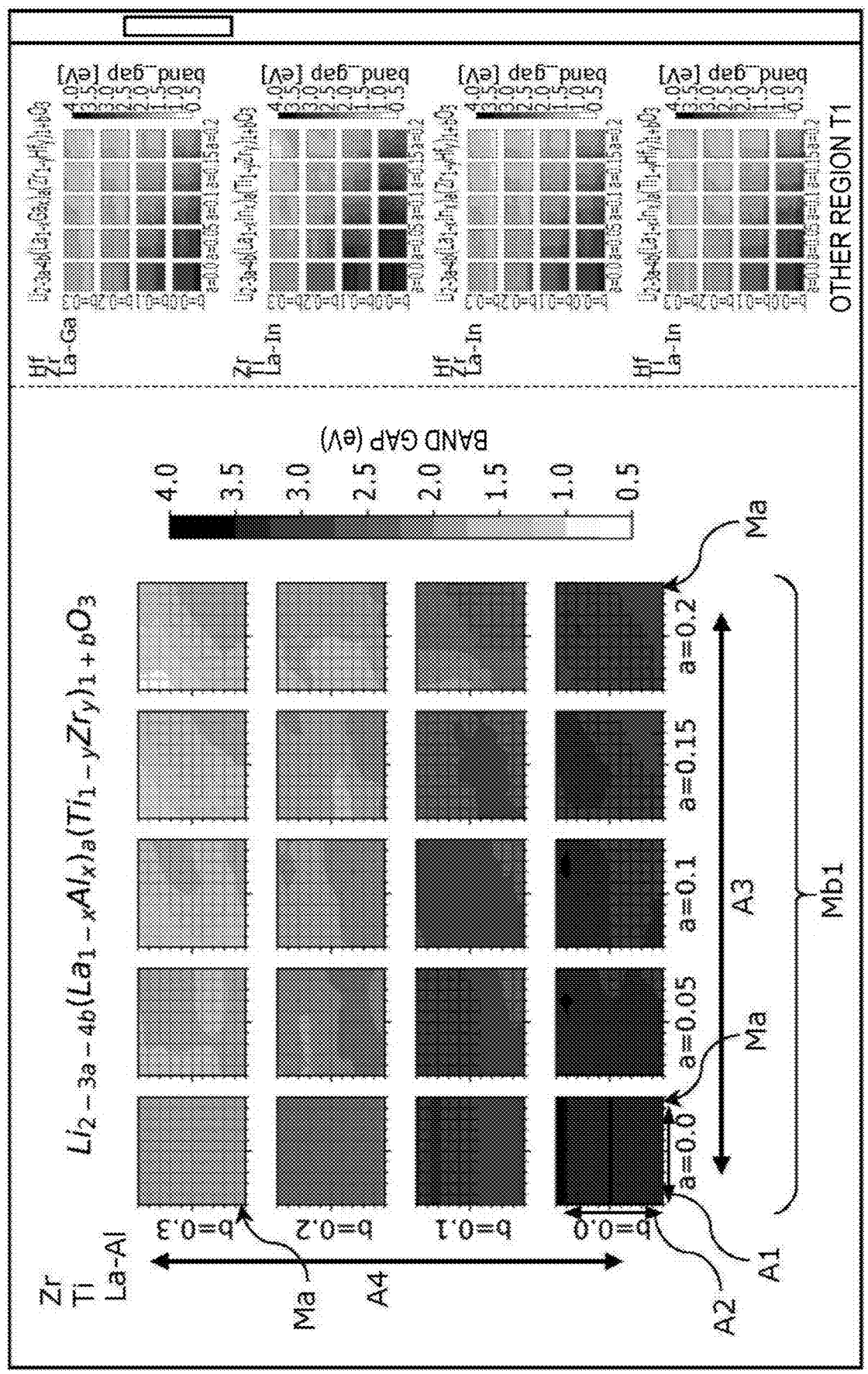
FIG. 7 is a diagram illustrating color maps and a first array map used when displaying a property of a compound.

FIG. 7 is a diagram illustrating the color maps Ma and the first array map Mb1 used when displaying a property of a compound. The property display device 1 of the present embodiment forms a single image containing the color maps Ma which are square plots and the first array map Mb1 in which the color maps Ma are arranged, and expresses an overall picture of a property of the compound. Note that a square plot refers to a color map expressed by two independent variables x and y.

The color maps Ma are images in which differences in the property of the compound are expressed by being converted into colors. The property of the compound is the band gap (eV), which is one of the properties of a solid electrolyte, for example. Although the color maps Ma in FIG. 7 are illustrated in grayscale, the actual colors are such that black in FIG. 7 is red in the actual color maps, white in FIG. 7 is blue in the actual color maps, and intermediate shades between black and white in FIG. 7 are white in the actual color maps. For example, by setting white to a standard for the property value in the actual color maps, it is possible to see at a glance whether a prescribed region of the color maps Ma is below or above the standard.

The color maps Ma illustrated in FIG. 7 have a coordinate axis A1 as the horizontal axis and a coordinate axis A2 as the vertical axis. The first array map Mb1 is in a matrix form and has an array direction axis A3 as the horizontal axis and an array direction axis A4 as the vertical axis.

FIG. 8 is a diagram illustrating an example of assigning search variables to the coordinate axes A1 and A2 of the color maps Ma and the array direction axes A3 and A4 of the first array map Mb1.

The display format determination unit 16 assigns the two variables with the highest and second-highest priority from among the continuous variables, discrete variables, and category variables to the two coordinate axes A1 and A2 of the color maps Ma. In FIG. 8, the continuous variable x is assigned to the coordinate axis A1, and the continuous variable y is assigned to the coordinate axis A2.

Figure 9:
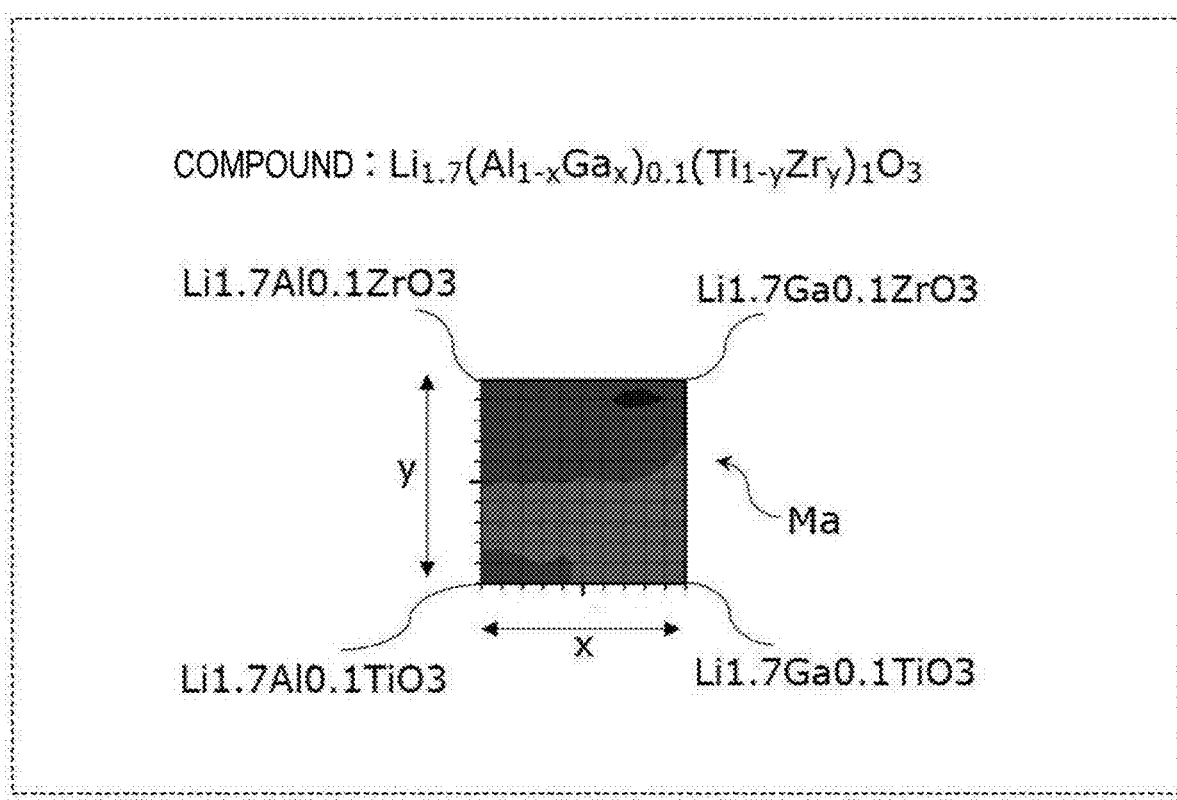
FIG. 9 is a diagram illustrating an image of a state in which continuous variables are assigned to the coordinate axes of the color maps.

FIG. 9 is a diagram illustrating an image of a state in which the continuous variables x and y are assigned to the coordinate axes A1 and A2 of a color map Ma. In FIG. 9, the compound in the lower-left corner of the color map Ma is $Li_{1.7}Al_{0.1}TiO_3$, the compound in the lower-right corner is $Li_{1.7}Ga_{0.1}TiO_3$, the compound in the upper-left corner is $Li_{1.7}Al_{0.1}ZrO_3$, and the compound in the upper-right corner is $Li_{1.7}Ga_{0.1}ZrO_3$. In this color map Ma, since the property value decreases toward the lower-right corner, it is easy to understand that if the ratio of Ga or the ratio of Ti is increased, the property value will decrease. In this way, by assigning the continuous variables x and y having large numbers of search data points to the coordinate axes A1 and A2 of the color map Ma, a property related to the continuous variables x and y can be analyzed in depth.

Moreover, as illustrated in FIG. 8, the display format determination unit 16 assigns two variables of high priority from among the variables that were not assigned to the coordinate axes A1 and A2 of the color maps Ma, namely the two variables with the third- and fourth-highest priority, to the two array direction axes A3 and A4 of the first array map Mb1. Specifically, the variable with the third-highest priority is assigned to the array direction axis A3 which is the column component of the first array map Mb1 expressed as a matrix, and the variable with the fourth-highest priority is assigned to the array direction axis A4 which is the row component of the first array map Mb1. In FIG. 8, the discrete variable a is assigned to the array direction axis A3, and the discrete variable b is assigned to the array direction axis A4.

Figure 10:
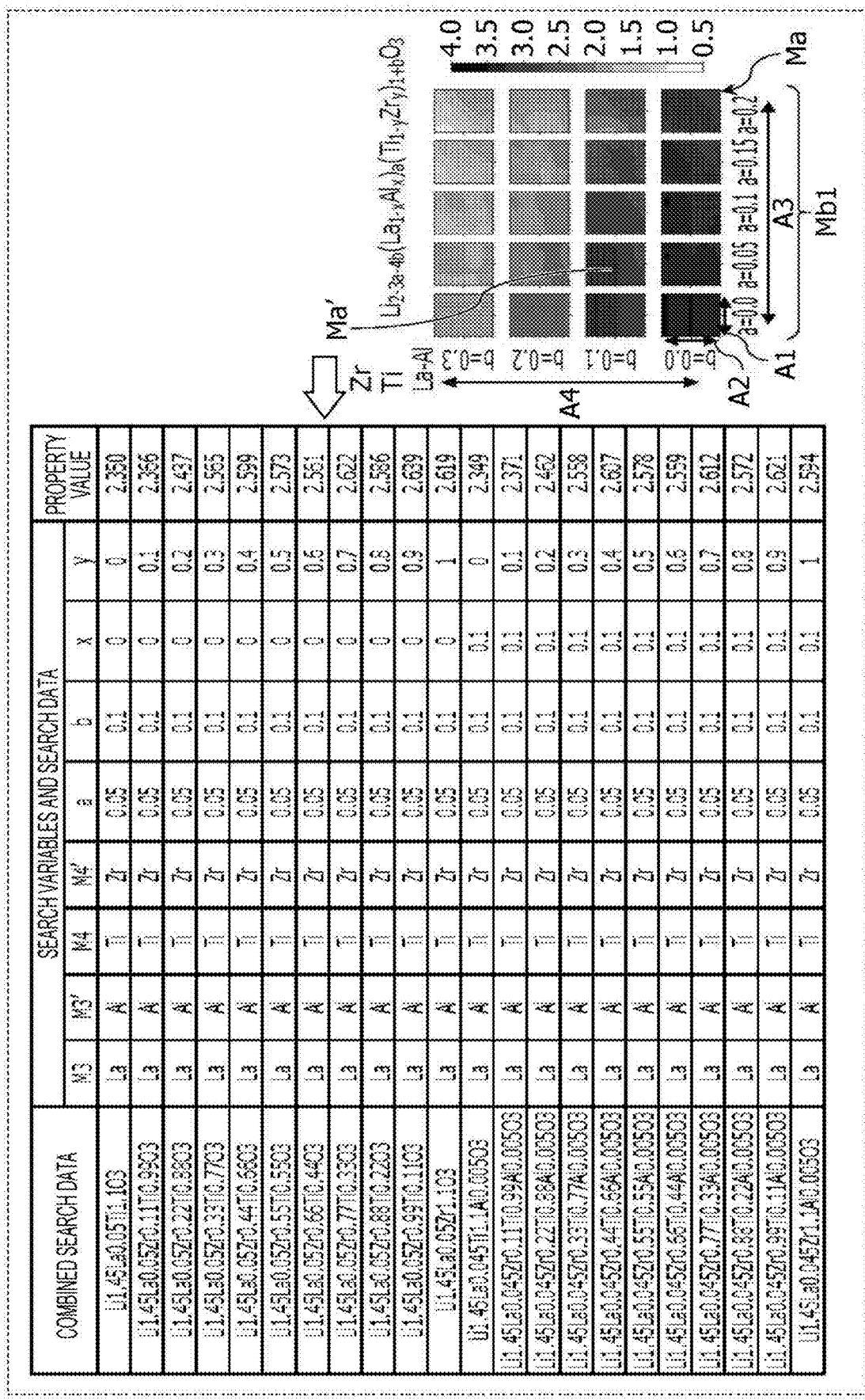
FIG. 10 is a diagram illustrating a prescribed color map in the first array map and a portion of the search data and property values corresponding to the prescribed color map.

FIG. 10 is a diagram illustrating a prescribed color map Ma' in the first array map Mb1 and a portion of the search data and property values corresponding to the prescribed color map Ma'. The search data indicates that M3=La, M3'=A1, M4=Ti and M4'=Zr, that a=0.0 and b=0.1, and that x and y are values from 0 to 1 in steps of 0.1.

Note that if there are other search variables that were not assigned to the coordinate axes A1, A2 and the array direction axes A3, A4 from among the search variables, the display format determination unit 16 may determine that images based on the other search variables are to be displayed in another region T1 (see FIG. 7) different from the color maps Ma and the first array map Mb1. For example, the display format determination unit 16 may cause the display of images based on the other search variables to be switched through the use of a scrollbar on the screen.

The display format determination unit 16 outputs the determined display format to the image processing unit 17.

The image processing unit 17 acquires the search data and property values outputted from the property value acquisition unit 14, and acquires the display format outputted from the display format determination unit 16. The image processing unit 17 generates an image indicating the property of the compound on the basis of the acquired search data, property values, and display format. Specifically, the image processing unit 17 generates the first array map Mb1 including the color maps Ma as a single image. That is, the image processing unit 17 visualizes information indicating the property of the compound on the basis of the acquired search data, property values, and display format. The image processing unit 17 outputs a signal expressing the generated image to the display unit 18.

Note that the image processing unit 17 may also divide up the search data into the search variables other than the search variables that are assigned to the coordinate axes A1 and A2 of the color maps Ma, and generate an image in which color maps are subdivided for each division of the divided-up search data.

Also, the image processing unit 17 may generate an image such that each property value corresponds in a 1:1 manner with the value of each search data point of the search variables assigned to the coordinate axes A1 and A2, or generate an image by interpolating between the data points. For example, in the case where the continuous variables x and y are assigned to the coordinate axes A1 and A2, there is 11×11 data, and therefore the image processing unit 17 may prepare 11×11 cells and generate an image in which a color is applied to each cell according to the property value of each cell. The image processing unit 17 may also generate an image in which points between the 11×11 data points are interpolated according to a known interpolation method (such as linear interpolation, bilinear interpolation, or bicubic interpolation, for example).

The display unit 18 is an output unit that outputs an image indicating the property of the compound. The display unit 18 is a display device such as a liquid crystal display (LCD) panel, for example, and displays an image on the basis of the signal outputted from the image processing unit 17.

Figure 11:
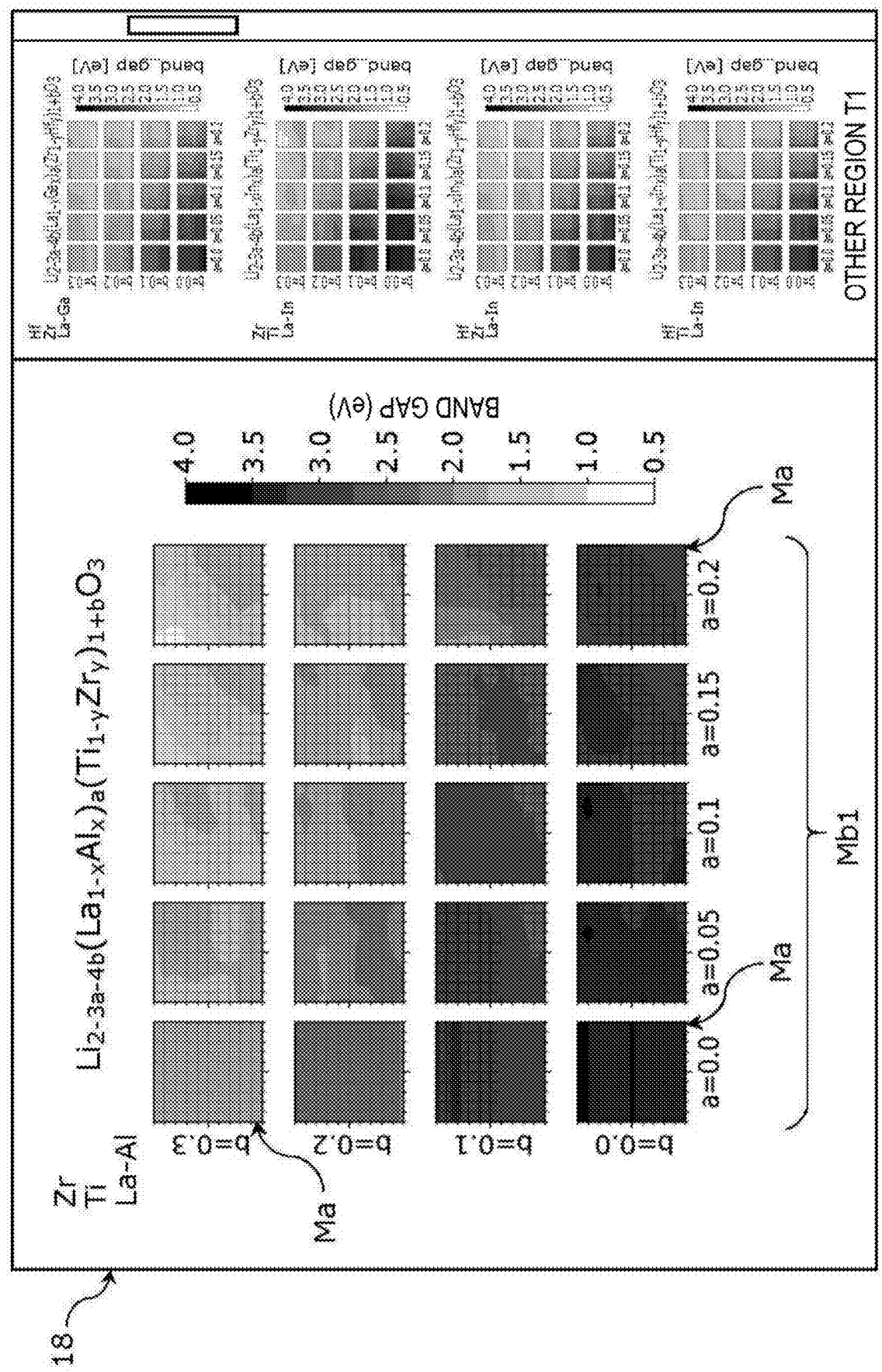
FIG. 11 is a diagram illustrating an example of an image displayed by the property display device of Embodiment 1.

FIG. 11 is a diagram illustrating an example of an image displayed on the display unit 18 of the property display system 5. In the image illustrated in FIG. 11, the first array map Mb1 is expressed in a state in which the color maps Ma are arrayed in a matrix of four rows and five columns. The image indicating the property of the compound may be an image in which the color maps Ma are arrayed as illustrated in FIG. 11, but may also be expressed in another display format. For example, the image indicating the property of the compound may include an image in which the compound to be searched is displayed in an upper part of the image, an image in which a color bar indicating the level of the property value is displayed, and an image in which the search variables and the search data are displayed.

[1-2. Processing Operations by Property Display Device and the Like]

Next, processing operations by the property display device 1 and the like according to Embodiment 1 will be described.

Figure 12:
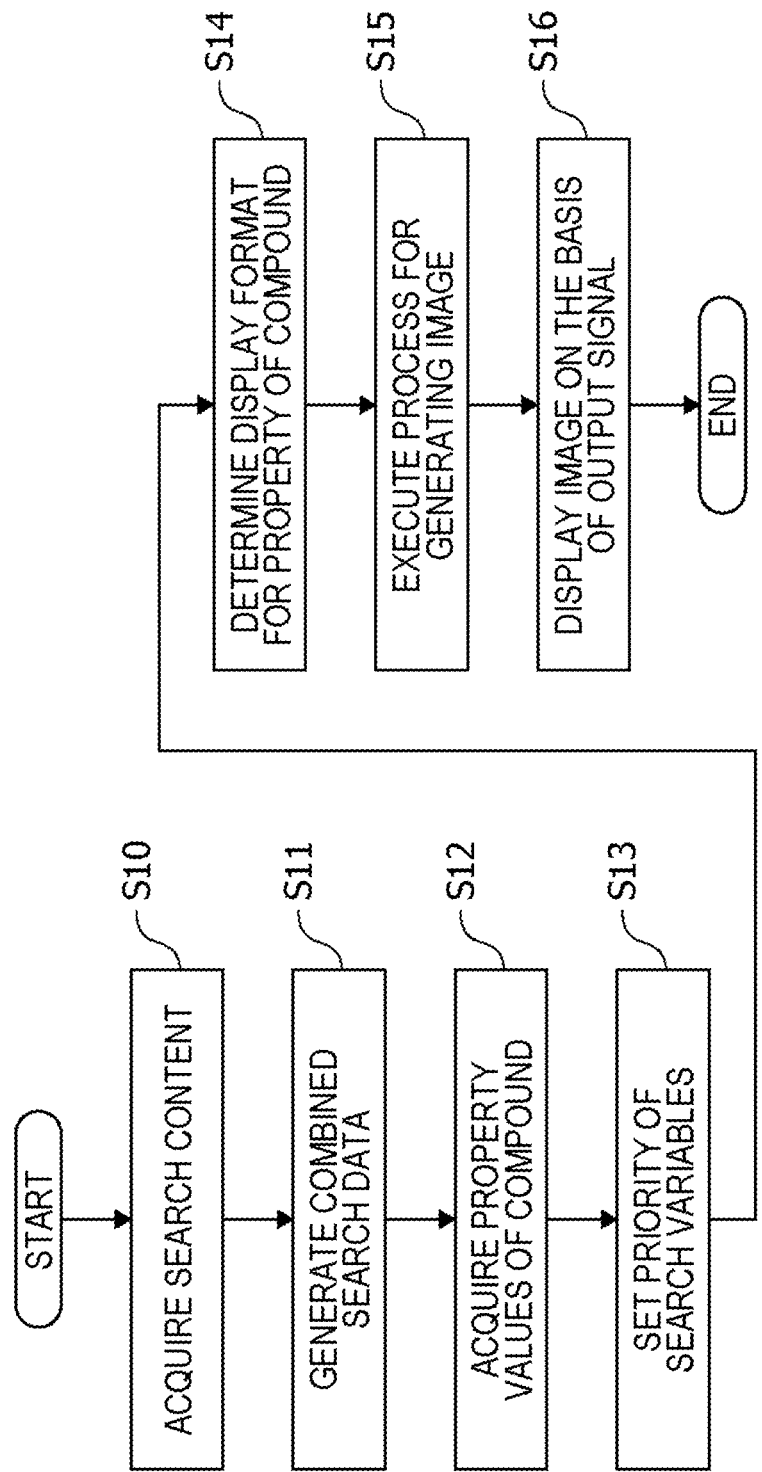
FIG. 12 is a flowchart illustrating an example of processing operations by a display unit included in the property display device and property display system according to Embodiment 1.

FIG. 12 is a flowchart illustrating an example of processing operations by the display unit 18 included in the property display device 1 and property display system 5.

First, the search content acquisition unit 11 acquires the search content outputted from the search content input unit 10 (step S10). The search content includes search variables and search data. The search content acquisition unit 11 outputs the acquired search content to each of the data editing unit 12 and the priority setting unit 15.

The data editing unit 12 receives the search content outputted from the search content acquisition unit 11 and generates combined search data in which all the search data is combined (step S11). The data editing unit 12 outputs the combined search data to the property value acquisition unit 14.

The property value acquisition unit 14 receives the combined search data outputted from the data editing unit 12 and acquires a predictor for calculating the property of the compound from the predictor database 13. The property value acquisition unit 14 inputs the combined search data into the predictor to calculate the property value of the compound corresponding to each data point, and thereby acquires property values (step S12). The property value acquisition unit 14 outputs the combined search data and the property values in association with each other to the image processing unit 17.

On the other hand, the priority setting unit 15 acquires the search content outputted from the search content acquisition unit 11 and sets the priority with respect to each search variable included in the search content (step S13). The search variables are provided for each of one or more continuous variables, one or more discrete variables, and one or more category variables. For example, from among the continuous variables x and y, the discrete variables a and b, and the category variables (M3, M3') and (M4, M4'), the continuous variables x and y have the greatest number of search data points, and therefore the priority setting unit 15 sets the highest priority for the continuous variables x and y. In addition, the priority setting unit 15 sets the priority of the discrete variables a and b higher than the priority of the category variables (M3, M3') and (M4, M4'). The priority setting unit 15 outputs the result of setting the priority to the display format determination unit 16.

The display format determination unit 16 determines the display format of the property of the compound on the basis of the result of setting the priority outputted from the priority setting unit 15 (step S14). Specifically, the display format determination unit 16 determines the display format of the property of the compound by assigning the search variables of high priority from among the search variables to the coordinate axes A1 and A2 of color maps Ma and assigning the search variables of lower priority than the search variables of high priority to the array direction axes A3 and A4 of a first array map Mb1. The display format determination unit 16 outputs the display format determined as above to the image processing unit 17.

Note that steps S13 and S14 may be executed in parallel with steps S11 and S12, or before or after steps S11 and S12.

The image processing unit 17 executes a process for generating an image indicating the property of the compound on the basis of the search data and property values outputted from the property value acquisition unit 14 and the display format outputted from the display format determination unit 16 (step S15). The image processing unit 17 is a visualization unit that visualizes the property of the compound. The visualization unit generates, on the basis of the acquired search data, property values, and visualization format, the first array map Mb1 including the color maps Ma as a single image. The image processing unit 17 outputs a signal expressing the generated image to the display unit 18.

The display unit 18 displays an image on the basis of the signal outputted from the image processing unit 17 (step S16). In the property display device 1 and the display unit 18, the display of the property of the compound is performed through the processing operations in steps S10 to S16.

Note that in the above embodiment, the priority is determined on the basis of factors such as the number, maximum value, and minimum value of the search variables, but the present disclosure is not limited thereto.

For example, the property value acquisition unit 14 may keep the search data fixed except for one of the search variables, calculate the variations in the property values when the one search variable is changed for all combinations of search variables with fixed search data, and take an average value of the variations of the property values for each of the continuous variables, the discrete variables, and the category variables, and the priority setting unit 15 may set a high priority for variables having a low average value of the variations of the property values from among the continuous variables, discrete variables, and category variables. In the above embodiment, the continuous variables x and y correspond to the variables having the lowest average value of the variations of the property values. When actually calculated, the average values of the variations of the property values are 'x': 0.0277, 'y': 0.0633, 'M3': 0.0900, 'a': 0.1343, 'M4': 0.2671, and 'b': 0.3055, and the continuous variables x and y have the smallest and second-smallest average values of the variations of the property values. The variables a, b, M3, and M4 have the third-smallest or smaller average values.

[1-3. Modification 1 of Embodiment 1]

Next, the property display device 1 according to Modification 1 of Embodiment 1 will be described. Modification 1 describes how the property of the compound is displayed when the assignment of the search variables to the coordinate axes A1, A2 and the array direction axes A3, A4 is changed.

The present modification will be described by taking the example of a case in which the compound to be searched is a solid electrolyte and the composition formula of the compound is indicated by the following formula (2).

$$Li_{2-3a-4b}(Al_{1-x}Ga_x)_a(Ti_{1-y}Zr_y)_{1+b}O_3 \qquad \text{Formula (2)}$$

FIG. 13 is a diagram illustrating an example of search content inputted into the property display device 1 according to Modification 1. In FIG. 13, search variables and search data contained in the search content are illustrated. The search variables in Modification 1 are expressed by a composition formula including the four variables x, y, a, and b.

Figure 14:
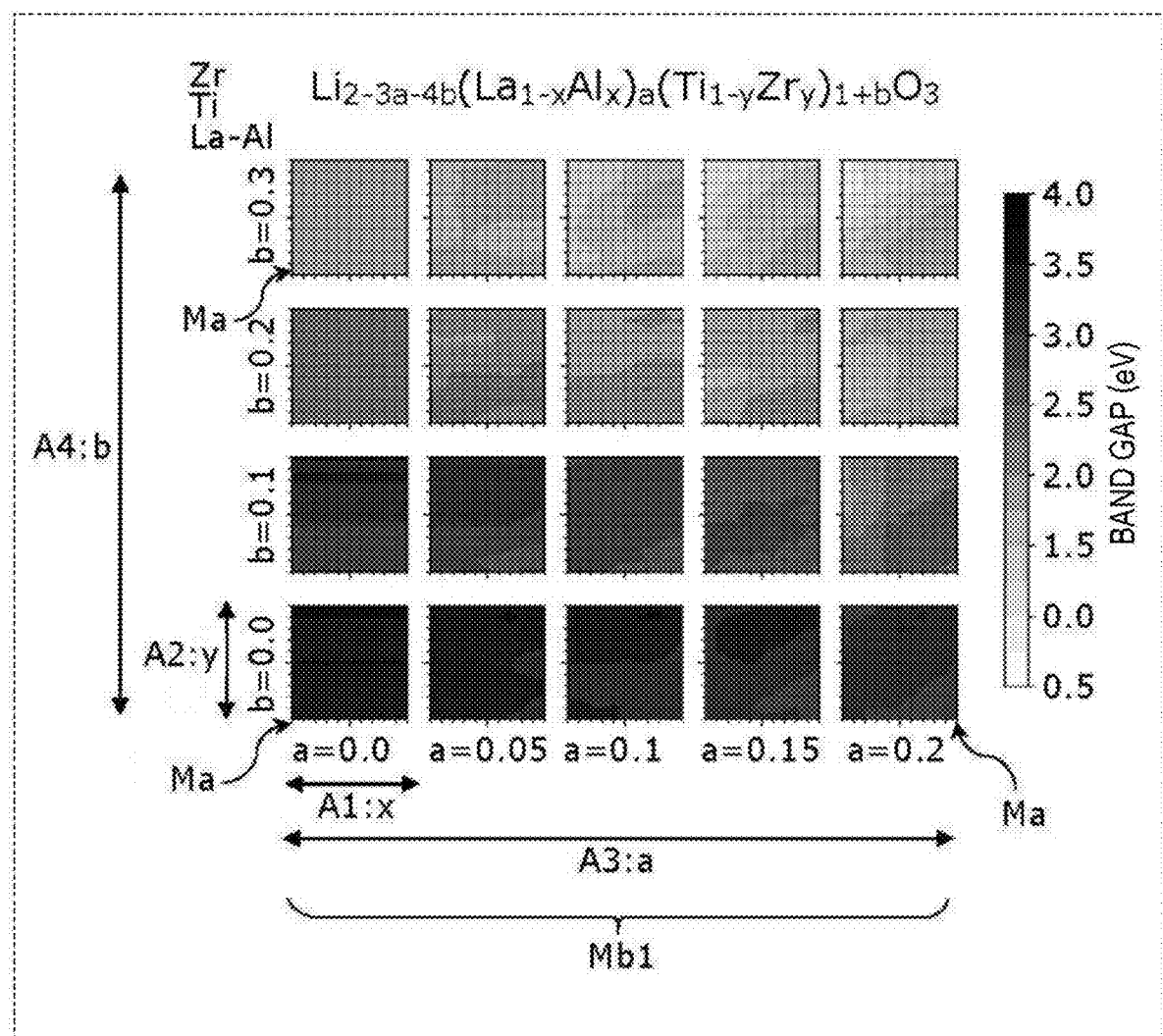
FIG. 14 is a diagram illustrating an example of an image displayed on the property display device according to Modification 1 of Embodiment 1.

FIG. 14 is a diagram illustrating an example of an image displayed on the property display device 1 according to Modification 1. FIG. 14 is similar to the display format of Embodiment 1, and is an example in which the variables x and y are respectively assigned to the coordinate axes A1 and A2 of each color map Ma, and the variables a and b are respectively assigned to the array direction axes A3 and A4 of the first array map Mb1. In FIG. 14, it can be seen that as the variables a and b increase, the property value decreases. It can also be seen that if the variables a and b are fixed, the property value increases or decreases as the variable x increases, for example.

Figure 15:
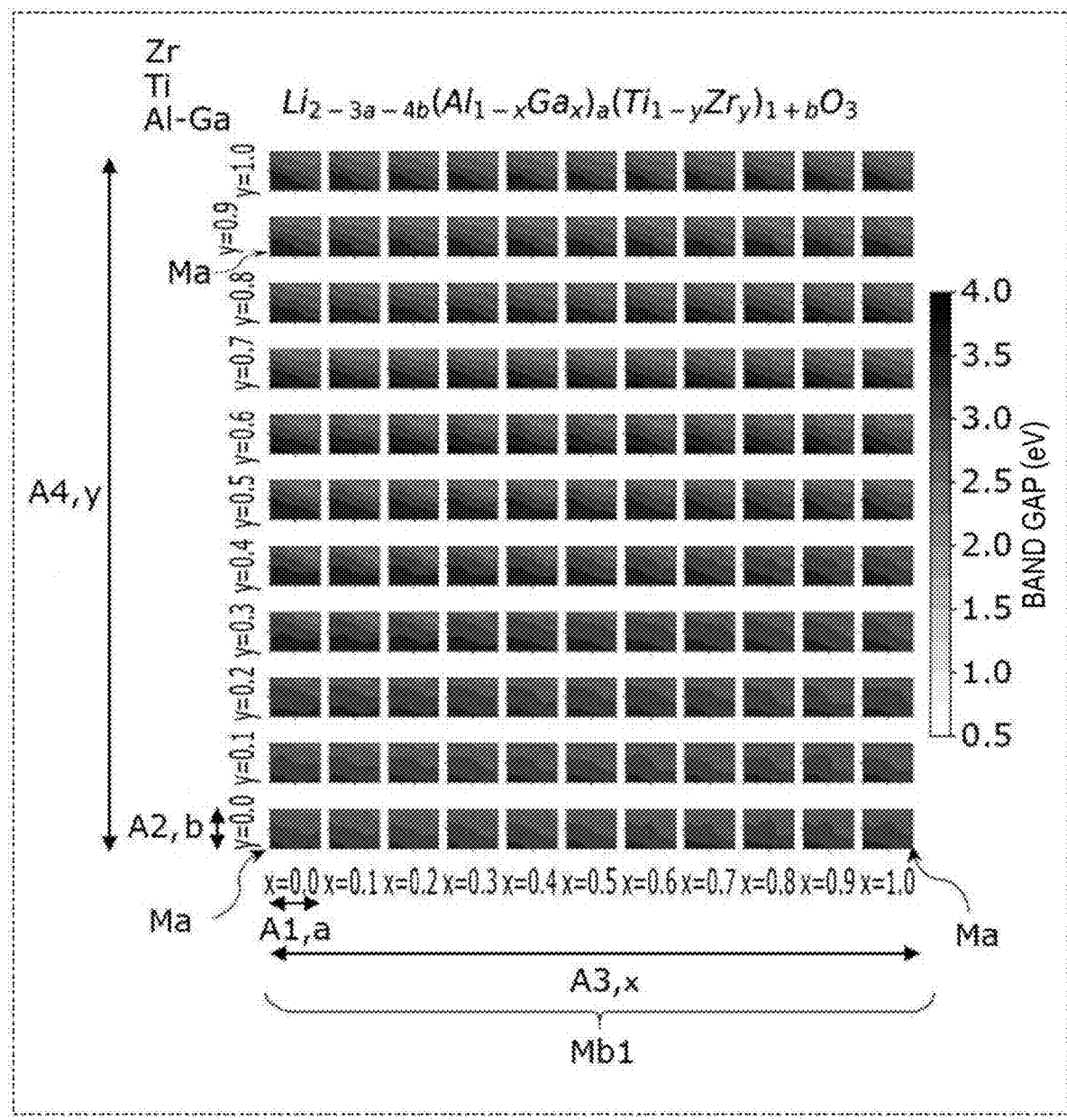
FIG. 15 is a diagram illustrating another example of an image displayed on the property display device according to Modification 1 of Embodiment 1.

FIG. 15 is a diagram illustrating another example of an image displayed on the property display device 1 according to Modification 1. FIG. 15 is an example in which the variables a and b are respectively assigned to the coordinate axes A1 and A2 of each color map Ma, and the variables x and y are respectively assigned to the array direction axes A3 and A4 of the first array map Mb1. In FIG. 15, it can be seen that as the variables a and b increase, the property value decreases. Also, the display format in FIG. 15 demonstrates that it is difficult to see changes in the property value associated with changes in the variable x or y.

By freely setting the priority like in the property display device 1 of Modification 1, an overall picture of a property of a compound can be recognized.

[1-4. Modification 2 of Embodiment 1]

Next, the property display device 1 according to Modification 2 of Embodiment 1 will be described. In Modification 2, an example will be described in which the property of the compound is displayed by using a second array map Mb2 in which multiple first array maps Mb1 are arranged.

Figure 16:
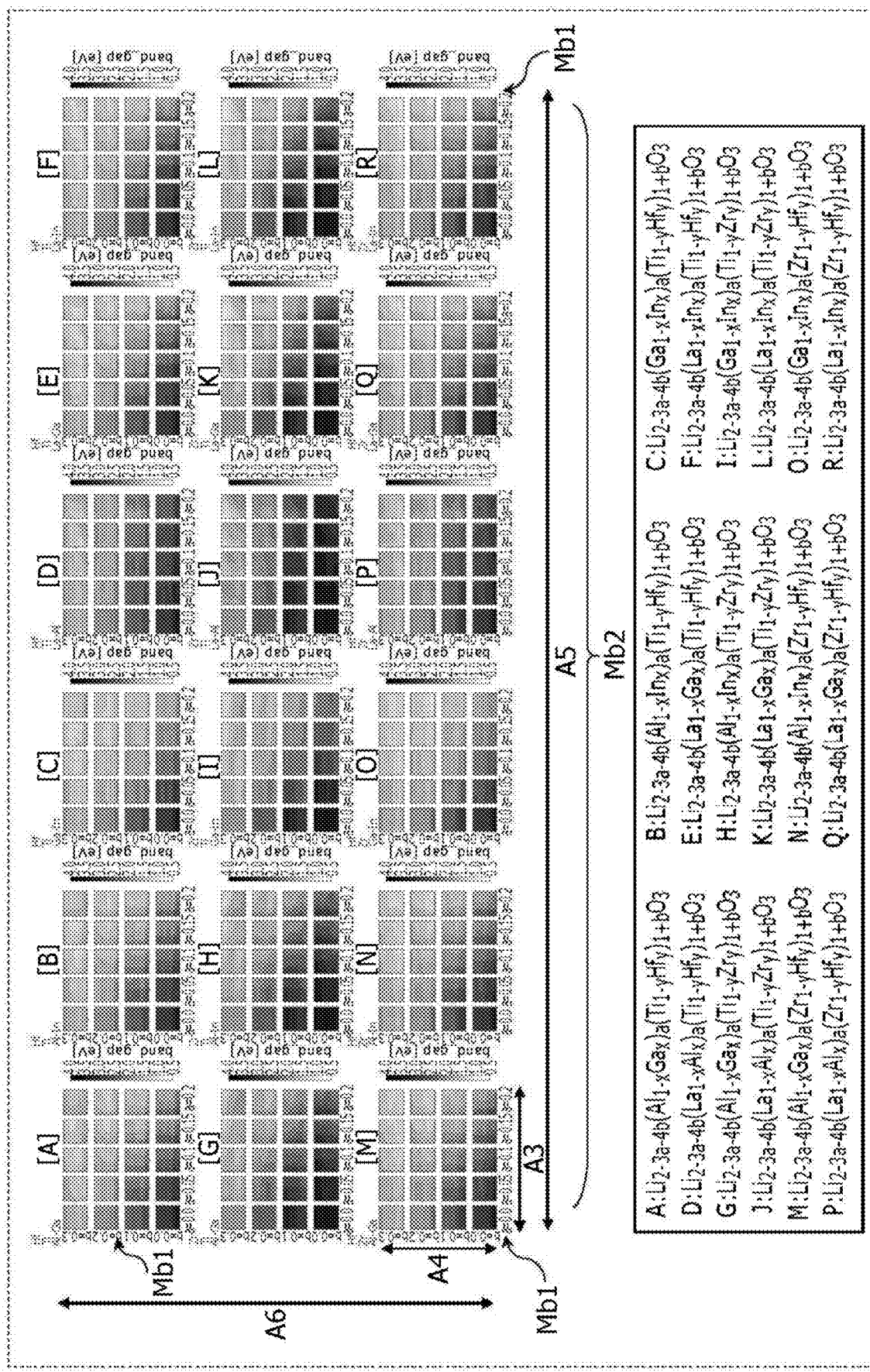
FIG. 16 is a diagram illustrating an example of an image displayed on a property display device according to Modification 2 of Embodiment 1.

FIG. 16 is a diagram illustrating an example of an image displayed on the property display device 1 according to Modification 2. In FIG. 16, [A] is $Li_{2-3a-4b}(Al_{1-x}Ga_x)_a(Ti_{1-y}Hf_y)_{1+b}O_3, \ldots,$ and [R] is $Li_{2-3a-4b}(La_{1-x}In_x)_a(Zr_{1-y}Hf_y)_{1+b}O_3$. To understand what [A], . . . , [R] represent, refer to the content inside the rectangular lines illustrated in the lower part of FIG. 16. The image displayed on the property display device 1 does not include the rectangular lines or the content A: $Li_{2-3a-4b}(Al_{1-x}Ga_x)_a(Ti_{1-y}Hf_y)_{1+b}O_3, \ldots,$ R: $Li_{2-3a-4b}(La_{1-x}In_x)_a(Zr_{1-y}Hf_y)_{1+b}O_3$ included inside the rectangular lines illustrated in the lower part of FIG. 16. FIG. 16 is illustrated in the above way so that the letters can be understood.

The second array map Mb2 illustrated in FIG. 16 is an array map in which multiple first array maps Mb1 are arranged. The second array map Mb2 is in a matrix form and has an array direction axis A5 as the horizontal axis and an array direction axis A6 as the vertical axis.

Like Embodiment 1, the display format determination unit 16 assigns the two variables with the highest and second-highest priority from among the continuous variables, discrete variables, and category variables to the two coordinate axes A1 and A2 of the color maps Ma. Moreover, the display format determination unit 16 assigns two search variables of high priority from among the variables that were not assigned to the coordinate axes A1 and A2 of the color maps Ma, namely the two search variables with the third- and fourth-highest priority, to the two array direction axes A3 and A4 of the first array maps Mb1. In FIG. 16, the two continuous variables x and y are assigned to the coordinate axes A1 and A2 of the color maps Ma, and the two discrete variables a and b are assigned to the array direction axes A3 and A4 of the first array maps Mb1.

Furthermore, the display format determination unit 16 of Modification 2 assigns the search variables with the fifth- and sixth-highest priority to the two array direction axes A5 and A6 of the second array map Mb2. For example, the search variable with the fifth-highest priority is assigned to the array direction axis A5 which is the column component of the second array map Mb2 expressed as a matrix, and the search variable with the sixth-highest priority is assigned to the array direction axis A6 which is the row component of the second array map Mb2. In FIG. 16, the category variable M3 and M3' having a high priority from among the category variables is assigned to the array direction axis A5, and the category variable M4 and M4' having the next-highest priority after M3 and M3' is assigned to the array direction axis A6.

According to the property display device 1 of Modification 2, an overall picture of a property of the compound can be recognized in relation to six variables, including continuous variables, discrete variables, category variables, and the like.

[1-5. Modification 3 of Embodiment 1]

Next, the property display device 1 according to Modification 3 of Embodiment 1 will be described. In Modification 3, an example will be described in which the color maps are ternary plots and category variables are assigned to the array direction axes A3 and A4 of the first array map Mb1.

The present modification will be described by taking the example of a case in which the compound to be searched is a semiconductor compound and the composition formula of the compound is indicated by the following formula (3).

$$M1(M2_{1-x-y}M2'_xM2''_y), \text{ where } x+y\leq 1 \quad \text{Formula (3)}$$

FIG. 17 is a diagram illustrating an example of search content inputted into the property display device 1 according to Modification 3. In FIG. 17, search variables and search data contained in the search content are illustrated. The search content of Modification 3 includes category variables and continuous variables, but does not include discrete variables.

Category variables are types of elements composing a compound, for example. In formula (3), M1 and (M2, M2', and M2") correspond to category variables. FIG. 17 illustrates an example in which one element from among the four elements of Se, O, As, and Nn is selected as an example of M1. The number of search data points for M1 is 4. Also, FIG. 17 illustrates an example in which three elements from among the five elements of Si, Ge, Zn, Cd, and In are selected as an example of the combination of M2, M2', and M2". The number of combinations of M2, M2', and M2", or in other words the number of search data points, is 10.

Continuous variables are numerical values for determining the composition ratio of a compound. Continuous variables have a large number of search data points compared to category variables, and are suited to cases where it is desirable to carry out in-depth analysis of changes in property values with respect to changes in the search data. Continuous variables are variables for which the search data has a maximum value of 1 and a minimum value of 0, for example. In addition, for continuous variables, the number of search data points may be 5 or more.

In formula (3), x and y each correspond to a continuous variable. The continuous variables x and y are correlated such that $x+y\leq 1$. For example, the ratio of M2 and the ratios of M2' and M2" expressed by the continuous variables x and y have a relationship whereby if the ratio of M2' or M2" is changed, the ratio of M2 also changes. The continuous variables x and y illustrated in FIG. 17 have a minimum value of 0.0, a maximum value of 1.0, and the number of search data points is 11. Each search data point of the continuous variables x and y may be expressed by listing all the data points, such as 0.0, 0.1, 0.2, . . . , 1.0, or may be expressed by indicating a data interval, such as a step size of 0.1.

Figure 18:
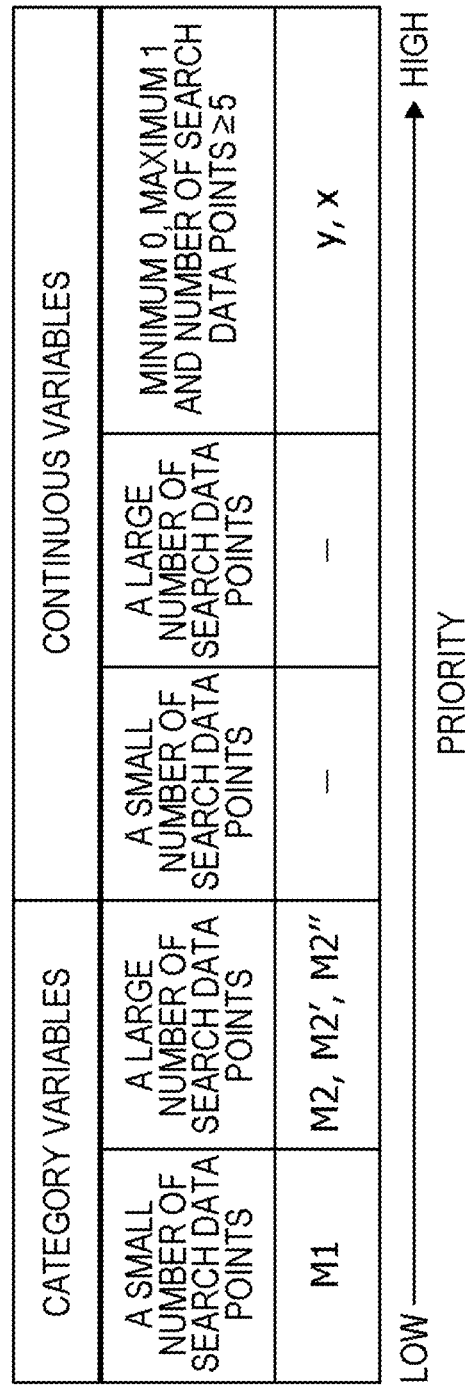
FIG. 18 is a diagram illustrating an example of the priority of search variables in Modification 3 of Embodiment 1.

FIG. 18 is a diagram illustrating an example of the priority of search variables. In FIG. 18, the priority is set higher for variables farther on the right side of the diagram. For example, from among the continuous variables x and y and the category variables M1 and (M2, M2', and M2"), the priority setting unit 15 sets the highest priority for the continuous variables x and y which have the greatest number of search data points.

Also, if multiple continuous variables exist, the priority setting unit 15 sets the priority for the continuous variables such that the larger the number of search data points a continuous variable has, the higher the priority is set. Note that as an exception, the priority setting unit 15 sets the highest priority for continuous variables in which the search data has a minimum value of 0, a maximum value of 1, and the number of search data points is equal to or greater than 5. Also, if the number of search data points is the same, the priority setting unit 15 sets the priority to the same level.

Also, if multiple category variables exist, the priority setting unit 15 sets the priority for the category variables such that the larger the number of search data points a category variable has, the higher the priority is set. Also, if the number of search data points is the same, the priority setting unit 15 sets the priority to the same level. In the example illustrated in FIG. 17, M1 is one element selected from among four elements, and therefore the number of search data points is 4, while (M2, M2', and M2") is a combination of three selected from among five elements, and therefore the number of search data points is 10. Consequently, the priority setting unit 15 sets the priority of (M2, M2', and M2") higher than M1.

The display format determination unit 16 determines the display format of the property of the compound on the basis of the result of setting the priority set by the priority setting unit 15. The display format determination unit 16 determines the display format of the property of the compound by assigning the search variables of high priority from among the search variables to coordinate axes A1a and A2a of color maps Maa and assigning the search variables of lower priority than the search variables of high priority to the array direction axes A3 and A4 of the first array map Mb1. Hereinafter, the color maps Maa, the first array map Mb1, and the like will be described.

Figure 19:
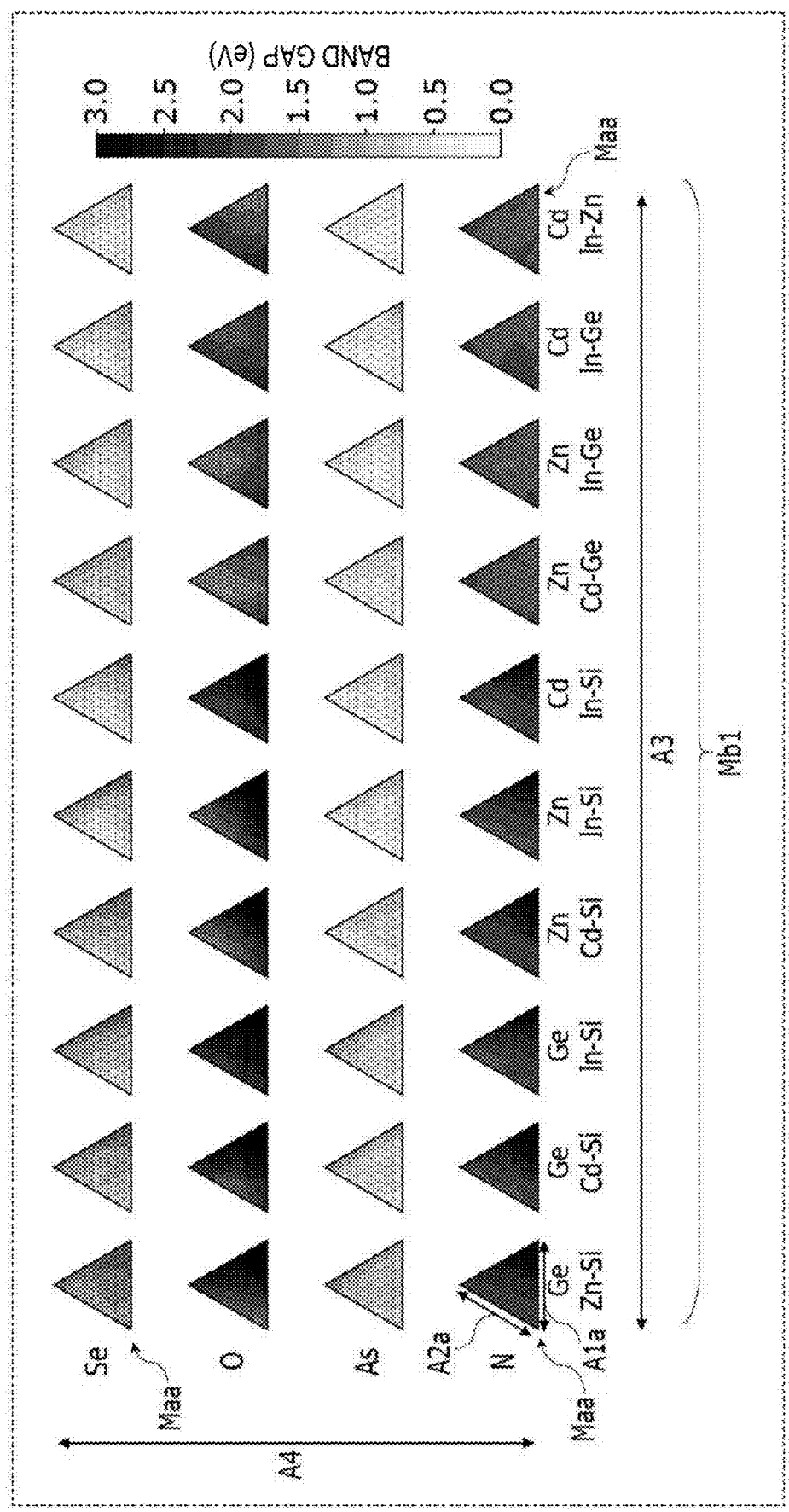
FIG. 19 is a diagram illustrating an example of assigning search variables to the coordinate axes of the color maps and the array direction axes of the first array map in Modification 3 of Embodiment 1.

FIG. 19 is a diagram illustrating color maps Maa and a first array map Mb1 used when displaying a property of a compound. In the case where the continuous variables x and y have a relationship where $x+y\leq 1$, ternary plots, for example, are used as the color maps Maa to be displayed. Note that a ternary plot refers to a color map expressed by three variables x, y, and z (where $x+y+z=1$).

The property display device 1 of the present modification forms a single image containing the color maps Maa and the first array map Mb1 in which the color maps Maa are arranged, and expresses an overall picture of a property of the compound.

The color maps Maa are images in which differences in the property of the compound are expressed by being converted into colors. The property of the compound is the band gap (eV), which is one of the properties of a semiconductor compound, for example. Although the color maps Maa in FIG. 19 are illustrated in grayscale, the actual colors are such that black in FIG. 19 is green in the actual color maps, white in FIG. 19 is red in the actual color maps, and intermediate shades between black and white in FIG. 19 are white in the actual color maps.

The color maps Maa illustrated in FIG. 19 have a coordinate axis A1a as the horizontal axis and a coordinate axis A2a which is inclined 60 degrees. The first array map Mb1 is in a matrix form and has an array direction axis A3 as the horizontal axis and an array direction axis A4 as the vertical axis.

FIG. 19 is a diagram illustrating an example of assigning search variables to the coordinate axes A1a and A2a of the color maps Maa and the array direction axes A3 and A4 of the first array map Mb1.

The display format determination unit 16 assigns the two variables with the highest and second-highest priority from among the continuous variables and category variables to the two coordinate axes A1a and A2a of the color maps Maa. In FIG. 19, the continuous variable x is assigned to the coordinate axis A1a, and the continuous variable y is assigned to the coordinate axis A2a.

As illustrated in FIG. 19, the display format determination unit 16 assigns two variables of high priority from among the variables that were not assigned to the coordinate axes A1a and A2a of the color maps Maa, namely the two variables with the third- and fourth-highest priority, to the two array direction axes A3 and A4 of the first array map Mb1. Specifically, the variable with the third-highest priority is assigned to the array direction axis A3 which is the column component of the first array map Mb1 expressed as a matrix, and the variable with the fourth-highest priority is assigned to the array direction axis A4 which is the row component of the first array map Mb1. In FIG. 19, the category variable (M2, M2', and M2") is assigned to the array direction axis A3, and the category variable M1 is assigned to the array direction axis A4.

The image processing unit 17 acquires the search data and property values outputted from the property value acquisition unit 14, and acquires the display format outputted from the display format determination unit 16. The image processing unit 17 generates an image indicating the property of the compound on the basis of the acquired search data, property values, and display format. Specifically, the image processing unit 17 generates the first array map Mb1 including the color maps Maa as a single image. That is, the image processing unit 17 visualizes information indicating the property of the compound on the basis of the acquired search data, property values, and display format. The image processing unit 17 outputs a signal expressing the generated image to the display unit 18. The display unit 18 displays an image on the basis of the signal outputted from the image processing unit 17.

Even in the case where the color maps Maa are ternary plots and the category variables are assigned to the array direction axes A3 and A4 of the first array map Mb1 like in the property display device 1 of Modification 3, an overall picture of a property of the compound can be recognized.

Note that when category variables are used for the array direction axes A3 and A4 of the first array map Mb1, the search data of the category variables may be arranged and displayed in any order. For example, the display format determination unit 16 may arrange the search data on the basis of the sort order of the search data in the acquired search variables. For example, in the case where the category variables are elements, the display format determination unit 16 may arrange the search data on the basis of physical properties or arrange the search data on the basis of the magnitude of the property values. Examples of physical properties include electronegativity and atomic number.

[1-6. Effects and the Like]

As above, the property display device 1 according to the present embodiment includes: the search content acquisition unit 11 that acquires search variables that determine the composition of a compound when searching for a property of the compound by changing the composition of the compound and search data indicating the values or ranges that the search variables take; the property value acquisition unit 14 that acquires property values of the compound corresponding to the search data; the priority setting unit 15 that sets the priority of the search variables; the display format determination unit 16 that determines the display format of the property of the compound by assigning the search variables of high priority from among the search variables to the coordinate axes A1 and A2 of the color maps Ma indicating the property of the compound and assigning the search variables of lower priority than the search variables of high priority to the array direction axes A3 and A4 of the first array map Mb1 in which the color maps Ma are arranged; and the image processing unit 17 that generates at least one first array map Mb1 as a single image on the basis of the search data, the property values, and the display format.

In this way, by assigning the search variables to the color maps Ma and the first array map Mb1 according to the priority of the search variables, the display format of the property of the compound can be determined appropriately. Moreover, by expressing the property of the compound with the first array map Mb1 that includes the color maps Ma, the property of the compound can be recognized with a single image. This configuration makes it possible to recognize an overall picture of a property of a compound when the composition of the compound is changed.

Additionally, the search variables may be provided for each of one or more continuous variables, one or more discrete variables, and one or more category variables, in which the continuous variables have a larger number of search data points than the discrete variables and the category variables, the priority setting unit 15 may set the highest priority for the continuous variables when setting the priority, and the display format determination unit 16 may assign the continuous variables to the coordinate axes of the color maps.

In this way, by setting the highest priority for the continuous variables having many search data points, the display format of the property of the compound can be determined appropriately. Also, by assigning the continuous variables to the color maps Ma, changes of the property corresponding to changes of the continuous variables can be recognized in the color maps Ma. This configuration makes it possible to recognize an overall picture of a property of a compound when the composition of the compound is changed.

Additionally, the category variables may be at least one of an element forming the compound or a compound synthesis method for synthesizing the compound, and each of the continuous variables and discrete variables may be at least one of a numerical value for determining a composition ratio of the compound or a compound synthesis method for synthesizing the compound.

This configuration makes it possible to recognize an overall picture of a property of the compound when the elements forming the compound, the composition ratio of the compound, and the compound synthesis method are changed.

Additionally, the continuous variables may be variables for which the search data has a maximum value 1 and a minimum value of 0, and the number of search data points is equal to or greater than 5.

With this configuration, the continuous variables can be set appropriately and the display format of the property of the compound can be determined appropriately. Also, the continuous variables can be assigned to the color maps Ma appropriately, and changes of the property corresponding to changes of the continuous variables can be recognized in the color maps Ma. This configuration makes it possible to recognize an overall picture of a property of a compound when the composition of the compound is changed.

Also, if multiple continuous variables exist, the priority setting unit 15 may set the priority for the continuous variables such that the larger the number of search data points a continuous variable has, the higher the priority is set.

In this way, by setting the priority higher for continuous variables having a larger number of search data points, the display format of the property of the compound can be determined appropriately. Also, the continuous variables of high priority can be assigned to the color maps Ma, and changes of the property corresponding to changes of the continuous variables can be recognized in the color maps Ma. This configuration makes it possible to recognize an overall picture of a property of a compound when the composition of the compound is changed.

Also, if multiple discrete variables exist, the priority setting unit 15 may set the priority for the discrete variables such that the larger the number of search data points a discrete variable has, the higher the priority is set.

In this way, by setting the priority higher for discrete variables having a larger number of search data points, the display format of the property of the compound can be determined appropriately. This configuration makes it possible to recognize an overall picture of a property of a compound when the composition of the compound is changed.

Also, if multiple category variables exist, the priority setting unit 15 may set the priority for the category variables such that the larger the number of search data points a category variable has, the higher the priority is set.

In this way, by setting the priority higher for category variables having a larger number of search data points, the display format of the property of the compound can be determined appropriately. This configuration makes it possible to recognize an overall picture of a property of a compound when the composition of the compound is changed.

Additionally, the display format determination unit 16 may assign the variables with the highest and second-highest priority from among the continuous variables, discrete variables, and category variables to the two coordinate axes A1 and A2 of the color maps Ma, and assign the variables with the third- and fourth-highest priority to the two array direction axes A3 and A4 of the first array map Mb1.

In this way, by assigning the search variables to the color maps Ma and the first array map Mb1 according to the priority of the search variables, the display format of the property of the compound can be determined appropriately. Moreover, by expressing the property of the compound with the first array map Mb1 that includes the color maps Ma, the property of the compound can be recognized with a single image. This configuration makes it possible to recognize an overall picture of a property of a compound when the composition of the compound is changed.

Also, the property value acquisition unit 14 may keep the search data fixed except for one of the search variables, calculate the variations in the property values when the one search variable is changed for all combinations of search variables with fixed search data, and take an average value of the variations of the property values for each of the continuous variables, the discrete variables, and the category variables, and the priority setting unit 15 may set the priority high for variables having a low average value of the variations of the property values from among the continuous variables, discrete variables, and category variables.

In this way, by raising the priority for variables having a low average value of the variations of the property values, the display format of the property of the compound can be determined appropriately. Also, variables with a lower average value of the variations of the property values can be assigned to the color maps Ma, and changes of the property corresponding to changes of the variables can be recognized in the color maps Ma. This configuration makes it possible to recognize an overall picture of a property of a compound when the composition of the compound is changed.

Also, the priority setting unit 15 may set the priority of the category variables lower than the search variables of low priority, and the display format determination unit 16 may assign the category variables not to the coordinate axes A1 and A2 of the color maps Ma or to the array direction axes A3 and A4 of the first array map Mb1, but instead to the other region T1 different from the color maps Ma and the first array map Mb1.

In this way, by setting the priority low for category variables, the display format of the property of the compound can be determined appropriately. Also, by assigning the category variables to the other region T1 different from the color maps Ma and the first array map Mb1, changes of the property corresponding to changes of the continuous variables or the discrete variables can be recognized appropriately. This configuration makes it possible to recognize an overall picture of a property of a compound when the composition of the compound is changed.

Also, if multiple category variables exist, the display format determination unit 16 may assign the category variables of high priority from among the category variables to the array direction axes A5 and A6 of the second array map Mb2 in which multiple first array maps Mb1 are arranged, and the image processing unit 17 may generate an image indicating the property of the compound on the basis of the search data, the property values, and the display format.

In this way, by assigning the category variables to the second array map Mb2, it is possible to recognize an overall picture of a property of a compound when the composition of the compound, including the category variables, is changed.

Additionally, the display format determination unit 16 may assign the variables with the highest and second-highest priority from among the continuous variables, discrete variables, and category variables to the two coordinate axes A1 and A2 of the color maps Ma, assign the variables with the third- and fourth-highest priority to the two array direction axes A3 and A4 of the first array map Mb1, and assign the variables with the fifth- and sixth-highest priority to the two array direction axes A5 and A6 of the second array map Mb2 in which multiple first array map Mb1 are arranged, and the image processing unit 17 may generate an image indicating the property of the compound on the basis of the search data, the property values, and the display format.

In this way, by assigning the search variables to the color maps Ma, the first array maps Mb1, and the second array map Mb2 according to the priority of the search variables, the display format of the property of the compound can be determined appropriately. Moreover, by expressing the property of the compound with the color maps Ma, the first array maps Mb1, and the second array map Mb2, the property of the compound can be recognized with a single image. This configuration makes it possible to recognize an overall picture of a property of a compound when the composition of the compound is changed.

Also, the property display device 1 may further include the data editing unit 12 that generates all combinations that the search data may take and generates combined search data, and the property value acquisition unit 14 may acquire the property values of the compound by calculating the property values with respect to the combined search data.

According to this configuration, the property values of the compound with respect to the combined search data can be acquired in a short time.

The property display device 1 according to the present embodiment includes: the search content acquisition unit 11 that acquires search variables that determine the composition of a compound when searching for a property of the compound by changing the composition of the compound and search data indicating the values or ranges that the search variables take; and the image processing unit 17 that generates an image indicating the property of the compound in a way such that search variables of high priority from among the search variables are assigned to the coordinate axes of color maps indicating the property of the compound and in a way such that search variables of lower priority than the search variables of high priority are assigned to the array direction axes of a first array map in which the color maps are arranged.

In this way, by assigning the search variables to the color maps and the first array map according to the priority of the search variables, the display format of the property of the compound can be determined appropriately. Moreover, by expressing the property of the compound with the first array map that includes the color maps, the property of the compound can be recognized with a single image. This configuration makes it possible to recognize an overall picture of a property of a compound when the composition of the compound is changed.

Also, the search variables may be provided for each of one or more continuous variables and one or more discrete variables having a lower number of search data points than the continuous variables, and the image processing unit 17 may generate an image indicating the property of the compound in a way such that two continuous variables are assigned to the two coordinate axes A1 and A2 of the color maps Ma expressed as square plots and in a way such that two discrete variables are assigned to the array direction axes A3 and A4 of the first array map Mb1 in which the color maps Ma are arranged.

In this way, by assigning the continuous variables and the discrete variables to the square-plot color maps Ma and the first array map Mb1, respectively, according to the priority of the search variables, the display format of the property of the compound can be determined appropriately. Moreover, by expressing the property of the compound with the first array map Mb1 that includes the color maps Ma, the property of the compound can be recognized with a single image. This configuration makes it possible to recognize an overall picture of a property of a compound when the composition of the compound is changed.

Also, the search variables may be provided for each of one or more continuous variables and one or more category variables having a lower number of search data points than the continuous variables, and the image processing unit 17 may generate an image indicating the property of the compound in a way such that two continuous variables are assigned to the two coordinate axes A1$a$ and A2$a$ of the color maps Maa expressed as ternary plots and in a way such that two category variables are assigned to the array direction axes A3 and A4 of the first array map Mb1 in which the color maps Maa are arranged.

In this way, by assigning the continuous variables and the category variables to the ternary-plot color maps Maa and the first array map Mb1, respectively, according to the priority of the search variables, the display format of the property of the compound can be determined appropriately. Moreover, by expressing the property of the compound with the first array map Mb1 that includes the color maps Maa, the property of the compound can be recognized with a single image. This configuration makes it possible to recognize an overall picture of a property of a compound when the composition of the compound is changed.

A property display method according to the present embodiment includes: acquiring search variables that determine the composition of a compound when searching for a property of the compound by changing the composition of the compound and search data indicating the values or ranges that the search variables take; acquiring property values of the compound corresponding to the search data; setting the priority of the search variables; determining the display format of the property of the compound by assigning the search variables of high priority from among the search variables to the coordinate axes A1 and A2 of the color maps Ma indicating the property of the compound and assigning the search variables of lower priority than the search variables of high priority to the array direction axes A3 and A4 of the first array map Mb1 in which the color maps Ma are arranged; and generating at least one first array map Mb1 as a single image on the basis of the search data, the property values, and the display format.

In this way, by assigning the search variables to the color maps Ma and the first array map Mb1 according to the priority of the search variables, the display format of the property of the compound can be determined appropriately. Moreover, by expressing the property of the compound with the first array map Mb1 that includes the color maps Ma, the property of the compound can be recognized with a single image. This configuration makes it possible to recognize an overall picture of a property of a compound when the composition of the compound is changed.

A non-transitory computer-readable medium according to the present embodiment stores a program for causing a computer to execute a process including: acquiring search variables that determine the composition of a compound when searching for a property of the compound by changing the composition of the compound and search data indicating the values or ranges that the search variables take; acquiring property values of the compound corresponding to the search data; setting the priority of the search variables; determining the display format of the property of the compound by assigning the search variables of high priority from among the search variables to the coordinate axes A1 and A2 of the color maps Ma indicating the property of the compound and assigning the search variables of lower priority than the search variables of high priority to the array direction axes A3 and A4 of the first array map Mb1 in which the color maps Ma are arranged; and generating at least one first array map Mb1 as a single image on the basis of the search data, the property values, and the display format.

According to the non-transitory computer-readable medium, it is possible to recognize an overall picture of a property of a compound when the composition of the compound is changed, similarly to the property display method.

Embodiment 2

[2-1. Configuration of Property Display Device and Property Display System]

Next, a property display device and property display system according to Embodiment 2 will be described. In Embodiment 2, an example in which the property display device corrects the display format will be described.

Figure 20:
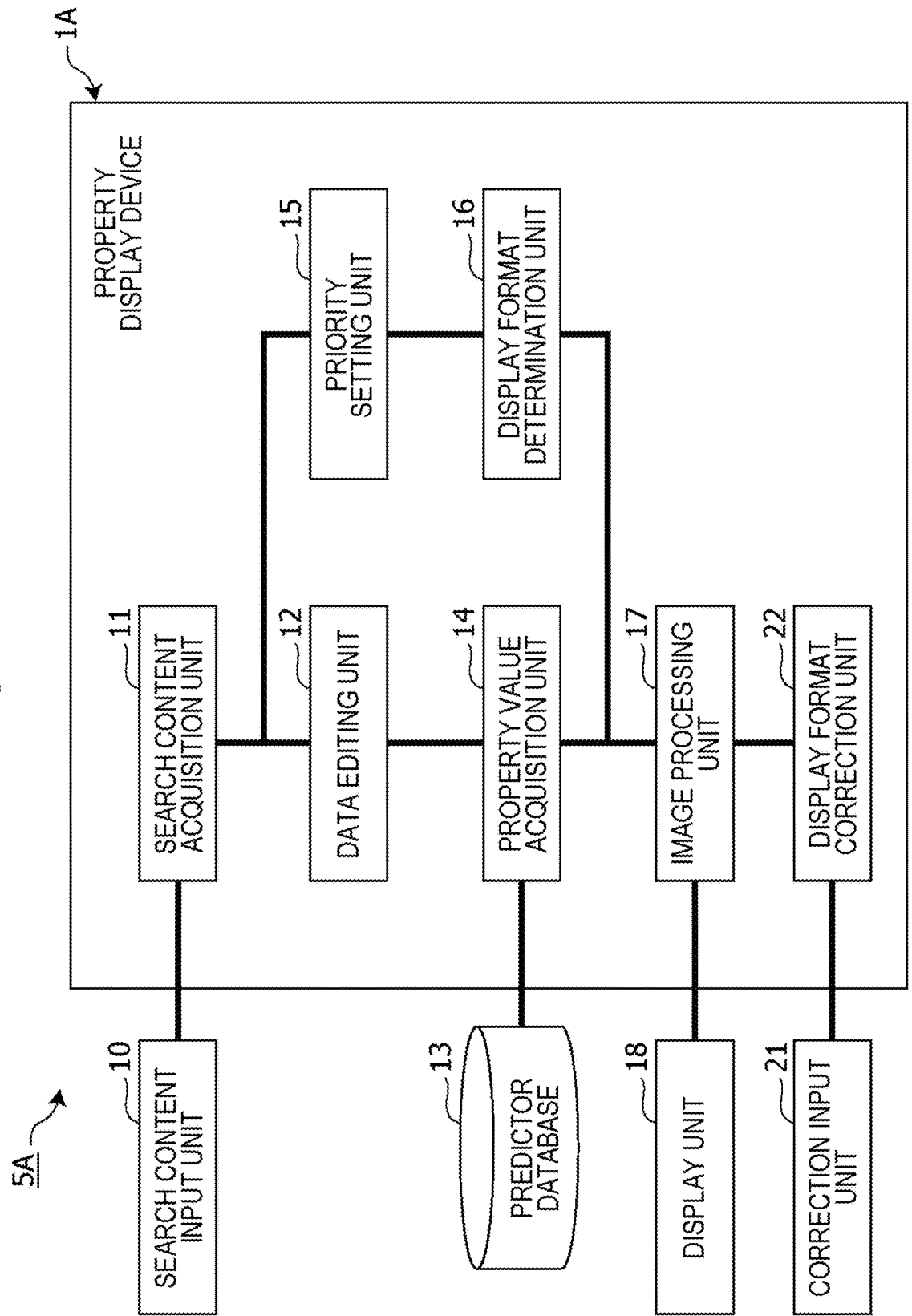
FIG. 20 is a block diagram illustrating a functional configuration of a property display system provided with a property display device according to Embodiment 2.

FIG. 20 is a block diagram illustrating a functional configuration of a property display system 5A provided with a property display device 1A according to Embodiment 2.

As illustrated in FIG. 20, the property display system 5A is provided with the property display device 1A, a search content input unit 10, a predictor database 13, a display unit 18, and a correction input unit 21. The property display device 1A is provided with a search content acquisition unit 11, a data editing unit 12, a property value acquisition unit 14, a priority setting unit 15, a display format determination unit 16, an image processing unit 17, and a display format correction unit 22.

The property display device 1A is configured by a processor such as a CPU, volatile memory and non-volatile memory, and a program stored in the non-volatile memory, for example. The functional configuration of the property display device 1A is achieved by executing the program.

The search content input unit 10, the predictor database 13, and the display unit 18 provided in the property display system 5A have the same configuration as in Embodiment 1, and therefore a description is omitted. The search content acquisition unit 11, the data editing unit 12, the property value acquisition unit 14, the priority setting unit 15, and the display format determination unit 16 provided in the property display device 1A have the same configuration as in Embodiment 1, and therefore a description is omitted. Hereinafter, the correction input unit 21 provided in the property display system 5A and the image processing unit 17 and display format correction unit 22 provided in the property display device 1A will be described. The image processing unit 17 in the present embodiment may be interpreted as also including the functions of the image processing unit 17 described in Embodiment 1.

The correction input unit 21 receives user input for correcting the display format of the property of the compound, and outputs the received correction input to the display format correction unit 22.

The display format correction unit 22 corrects the display format on the basis of the correction input outputted from the correction input unit 21, and outputs the correction content of the display format to the image processing unit 17.

The image processing unit 17 acquires the search data and property values outputted from the property value acquisition unit 14, and acquires the correction content of the display format outputted from the display format correction unit 22. The image processing unit 17 outputs a correction signal for correcting the display format to the display unit 18 on the basis of the acquired search data, property values, and correction content. Specifically, the image processing unit 17 receives correction content for correcting the assignment of the coordinate axes A1 and A2 of the color maps Ma or the array direction axes A3 and A4 of the first array map Mb1 from the display format correction unit 22, and generates an image indicating the property of the compound on the basis of the correction content.

Figure 21:
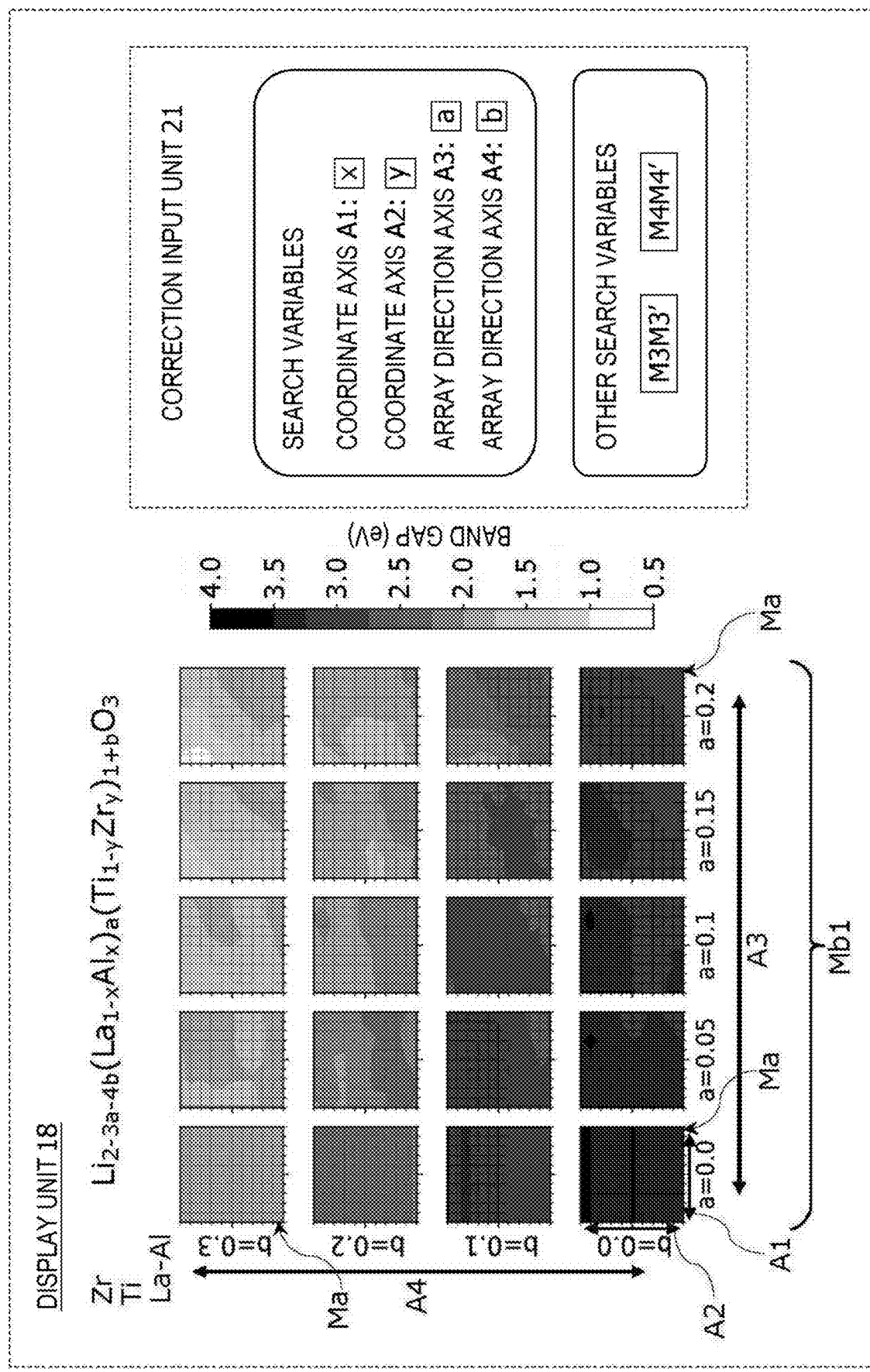
FIG. 21 is a diagram illustrating an example of a scene in which the display format of a property of a compound is corrected in the property display system of Embodiment 2.

FIG. 21 is a diagram illustrating an example of a scene in which the display format of a property of a compound is corrected in the property display system 5A.

In FIG. 21, a method of correcting the display format by drag and drop replacement of search variables on the screen of the display unit 18 is illustrated as the method for correcting the display format. For example, as illustrated in FIG. 21, the display format may be corrected by dragging and dropping one of the other search variables not assigned to the coordinate axes A1 and A2 or the array direction axes A3 and A4 onto the array direction axis A3 or A4 of the first array map Mb1.

When such correction input is received, the property display system 5A may immediately execute a correction of the display format based on the correction input. In addition, in the property display system 5A, a search variable evacuation area may be provided on the screen of the display unit 18, and the search variables may be temporarily evacuated to the evacuation area before replacing the search variables.

In the case of receiving correction input for assigning a category variable that had been one of the other search variables to the coordinate axis A1 or A2 of the color maps Ma, the property display system 5A may not correct the display format, and display, on the display unit 18, error information indicating that the display format cannot be corrected.

Figure 22:
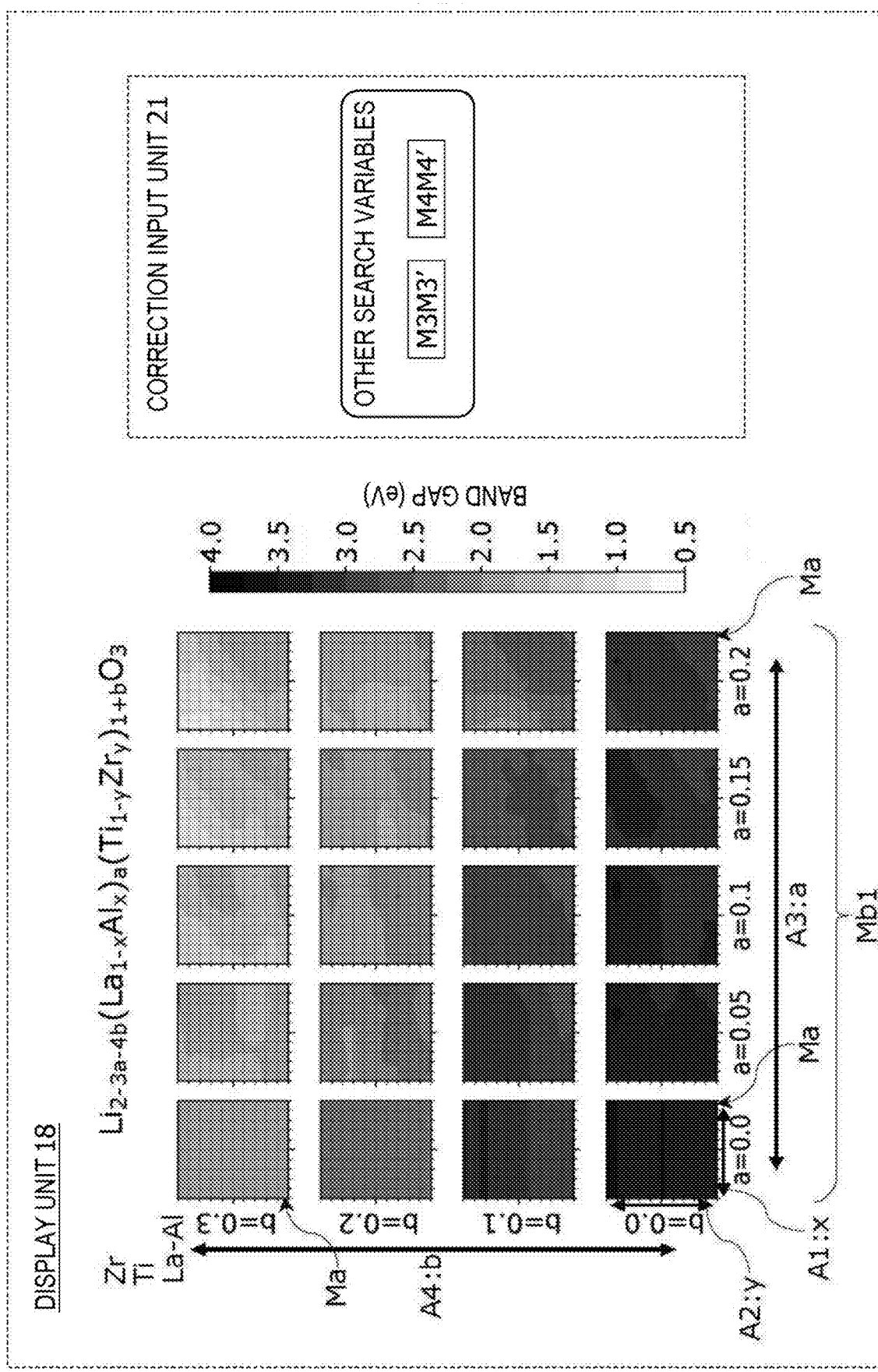
FIG. 22 is a diagram illustrating an example of displaying search variables on a screen of a display unit.
Figure 23:
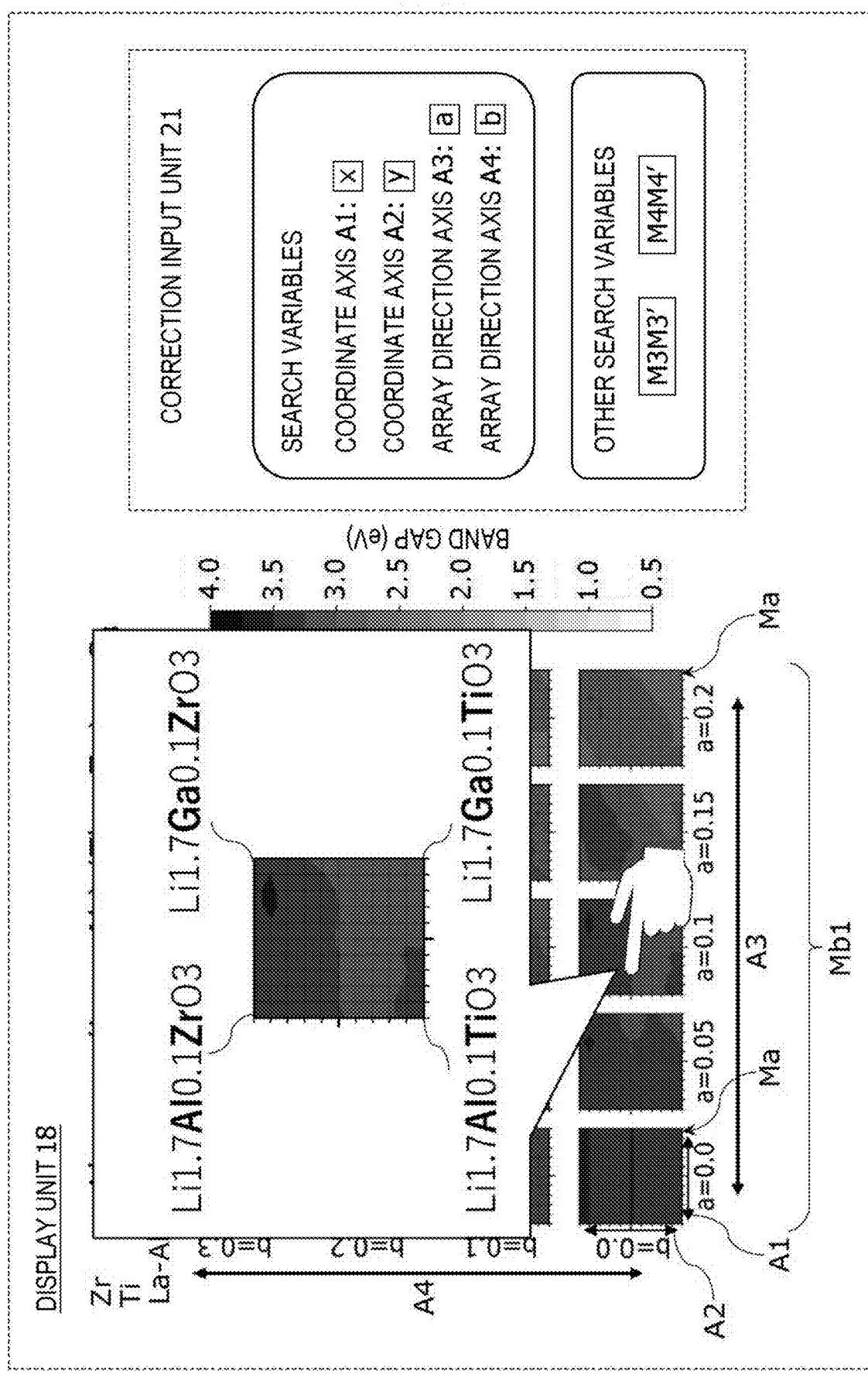
FIG. 23 is a diagram illustrating an example of displaying an enlarged view of a prescribed color map on the screen of a display unit.

FIG. 22 is a diagram illustrating an example of displaying search variables on the screen of the display unit 18. In FIG. 22, search variables are assigned respectively to the coordinate axes A1 and A2 and the array direction axes A3 and A4. FIG. 23 is a diagram illustrating an example of displaying an enlarged view of a prescribed color map Ma on the screen of the display unit 18. In FIG. 23, compounds corresponding to the four corners (lower-left corner, lower-right corner, upper-left corner, and upper-right corner) of the color map Ma are illustrated. The display formats in FIGS. 22 and 23 make it possible to recognize the currently displayed search content more easily and correct the display format appropriately.

[2-2. Processing Operations by Property Display Device and the Like]

Next, processing operations by the property display device 1A and the like according to Embodiment 2 will be described.

Figure 24:
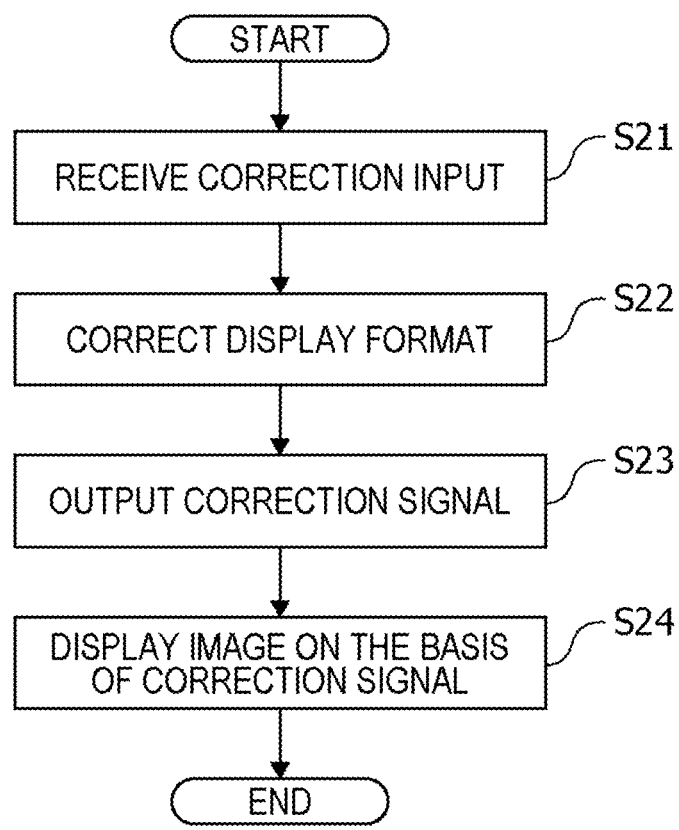
FIG. 24 is a flowchart illustrating an example of processing operations by a display unit included in the property display device and property display system according to Embodiment 2.

FIG. 24 is a flowchart illustrating an example of processing operations by the display unit 18 included in the property display device 1A and property display system 5A according to Embodiment 2. FIGS. 25A, 25B, 25C, and 25D are diagrams that sequentially illustrate scenes in which the display format of a property of a compound is corrected in the property display device 1A.

Figure 25A:
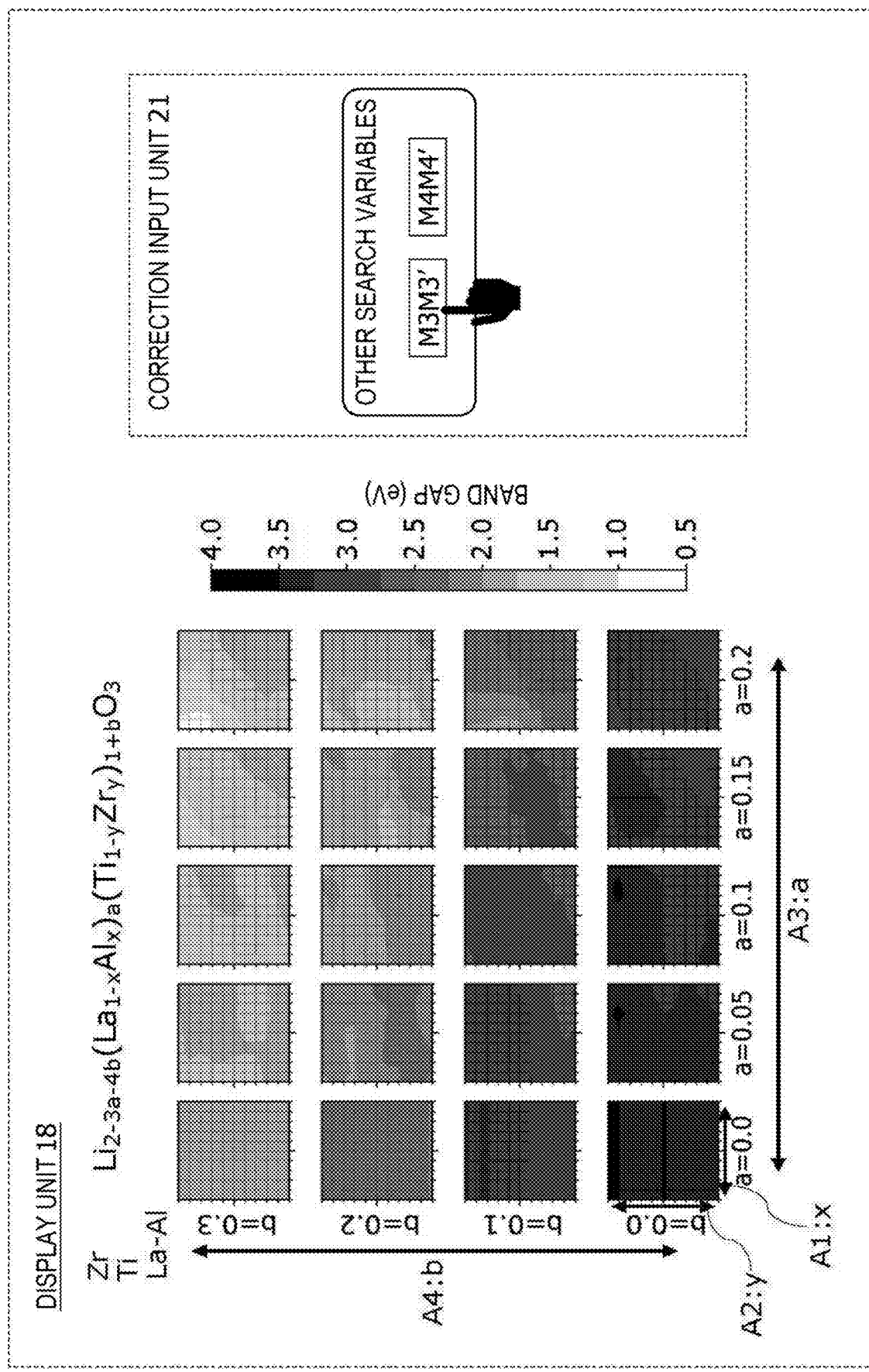
FIG. 25A is a diagram illustrating a scene in which the display format of a search variable is corrected in the property display device according to Embodiment 2.
Figure 25B:
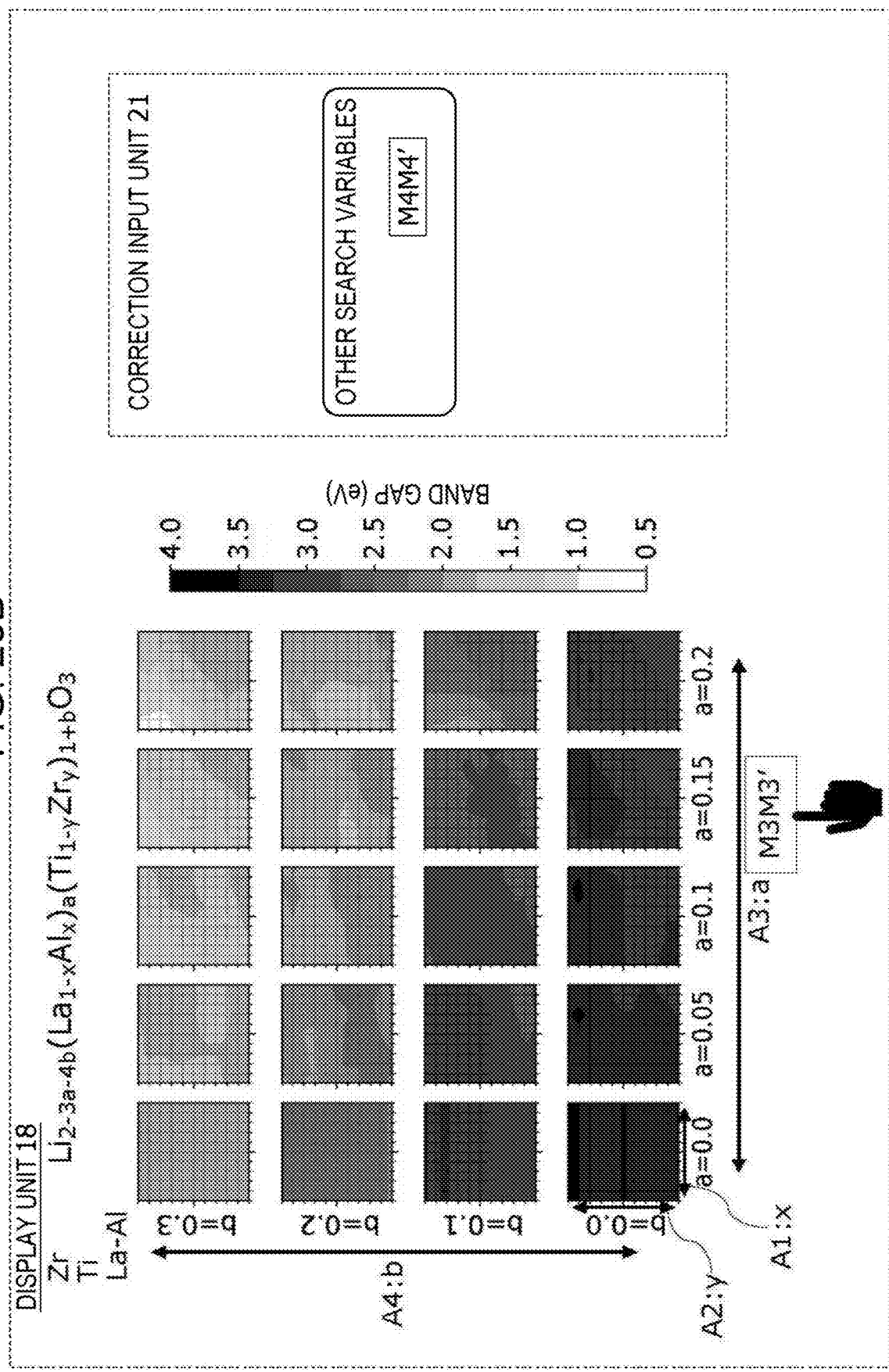
FIG. 25B is a continuation of FIG. 25A, and illustrates a scene in which the display format of a search variable is corrected.
Figure 25C:
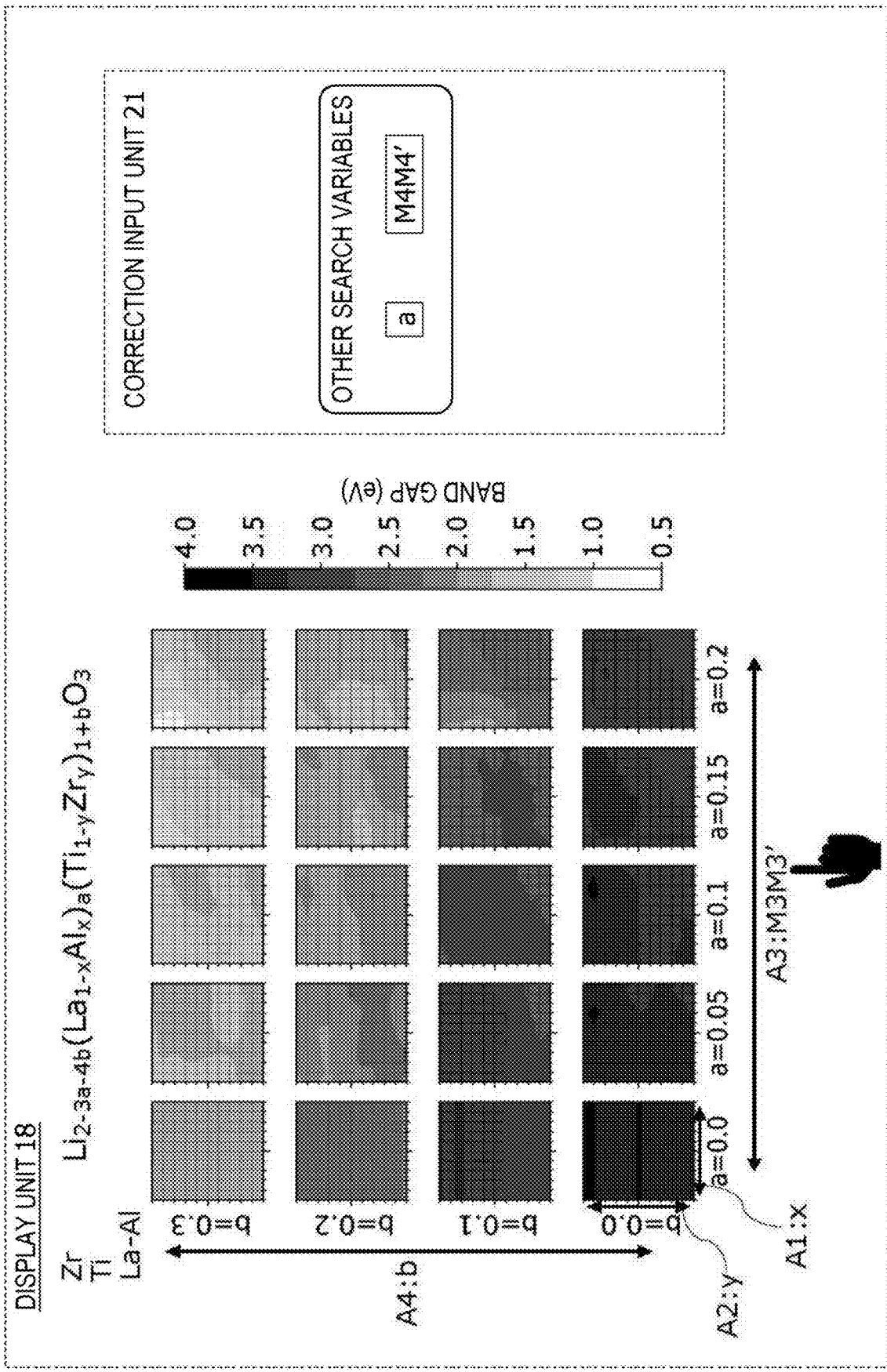
FIG. 25C is a continuation of FIG. 25B, and illustrates a scene in which the display format of a search variable is corrected.
Figure 25D:
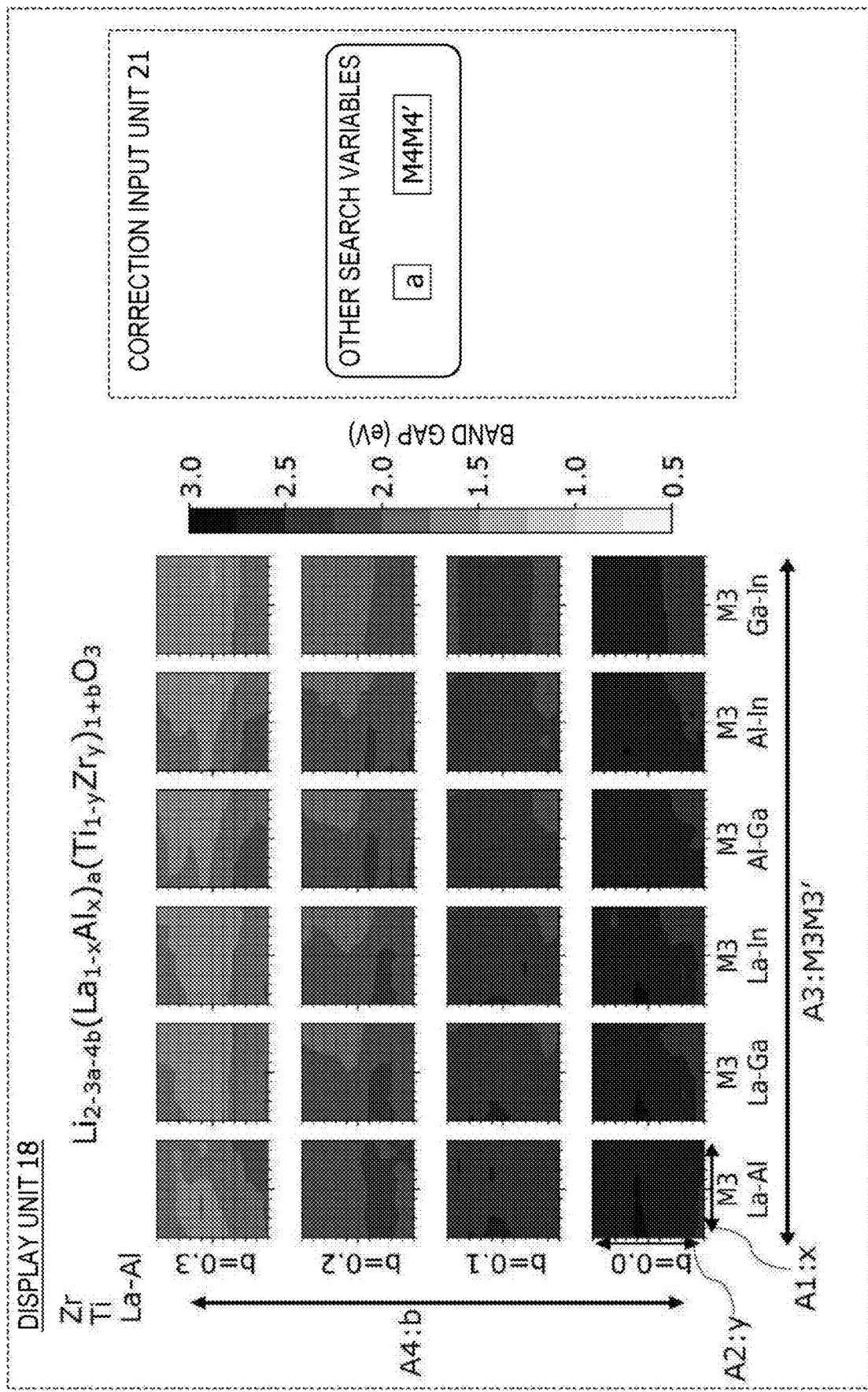
FIG. 25D is a continuation of FIG. 25C, and illustrates a scene in which the display format of a search variable is corrected.

First, the correction input unit 21 receives correction input for correcting the display format for displaying the property of the compound (S21). For example, as illustrated in FIG. 25A, a category variable (M3 and M3') that was not assigned to any of the coordinate axes A1 and A2 or the array direction axes A3 and A4 is selected by dragging, and as illustrated in FIG. 25B, the category variable (M3 and M3') is placed onto the array direction axis A3 of the first array map Mb1. Thereafter, as illustrated in FIG. 25C, the category variable (M3 and M3') is dropped onto the array direction axis A3 to replace the search variable on the array direction axis A3.

The correction input unit 21 outputs correction input received as above to the display format correction unit 22.

The display format correction unit 22 corrects the display format on the basis of the correction input outputted from the correction input unit 21 (S22), and outputs the correction content to the image processing unit 17.

The image processing unit 17 acquires the search data and property values outputted from the property value acquisition unit 14, and acquires the correction content outputted from the display format correction unit 22. The image processing unit 17 outputs a correction signal for correcting the display format to the display unit 18 on the basis of the acquired search data, property values, and correction content (S23).

The display unit 18 displays an image on the basis of the correction signal outputted from the image processing unit 17 (step S24). For example, in FIG. 25D, the search variable on the array direction axis A3 has been replaced, the first array map Mb1 has become four rows by six columns, and the property of the compound is being displayed on the basis of the corrected display format.

In the property display device 1A, the display format is corrected and the like according to steps S21 to S23. Note that the process of steps S21 to S23 may be executed multiple times according to user input.

[2-3. Effects and the Like]

In the property display device 1A of Embodiment 2, too, by assigning the search variables to the color maps Ma and the first array map Mb1 according to the priority of the search variables, the display format of the property of the compound can be determined appropriately. Moreover, by expressing the property of the compound with the first array map Mb1 that includes the color maps Ma, the property of the compound can be recognized with a single image. This configuration makes it possible to recognize an overall picture of a property of a compound when the composition of the compound is changed.

Also, the property display device 1A may further include the display format correction unit 22 that corrects the display format of the property of the compound, and if the image processing unit 17 receives correction content for correcting the assignment of the coordinate axes A1 and A2 of the color maps Ma or the array direction axes A3 and A4 of the first array map Mb1 from the display format correction unit 22, the image processing unit 17 may generate an image indicating the property of the compound on the basis of the correction content.

This configuration makes it possible to correct the display format of the property of the compound appropriately on the basis of the correction input, and recognize an overall picture of the property of the compound.

Embodiment 3

[3-1. Configuration of Property Display Device and Property Display System]

A property display device and property display system according to Embodiment 3 will be described. In Embodiment 3, an example in which the property display device does not have a function for editing the search data or a function for calculating the property values will be described.

Figure 26:
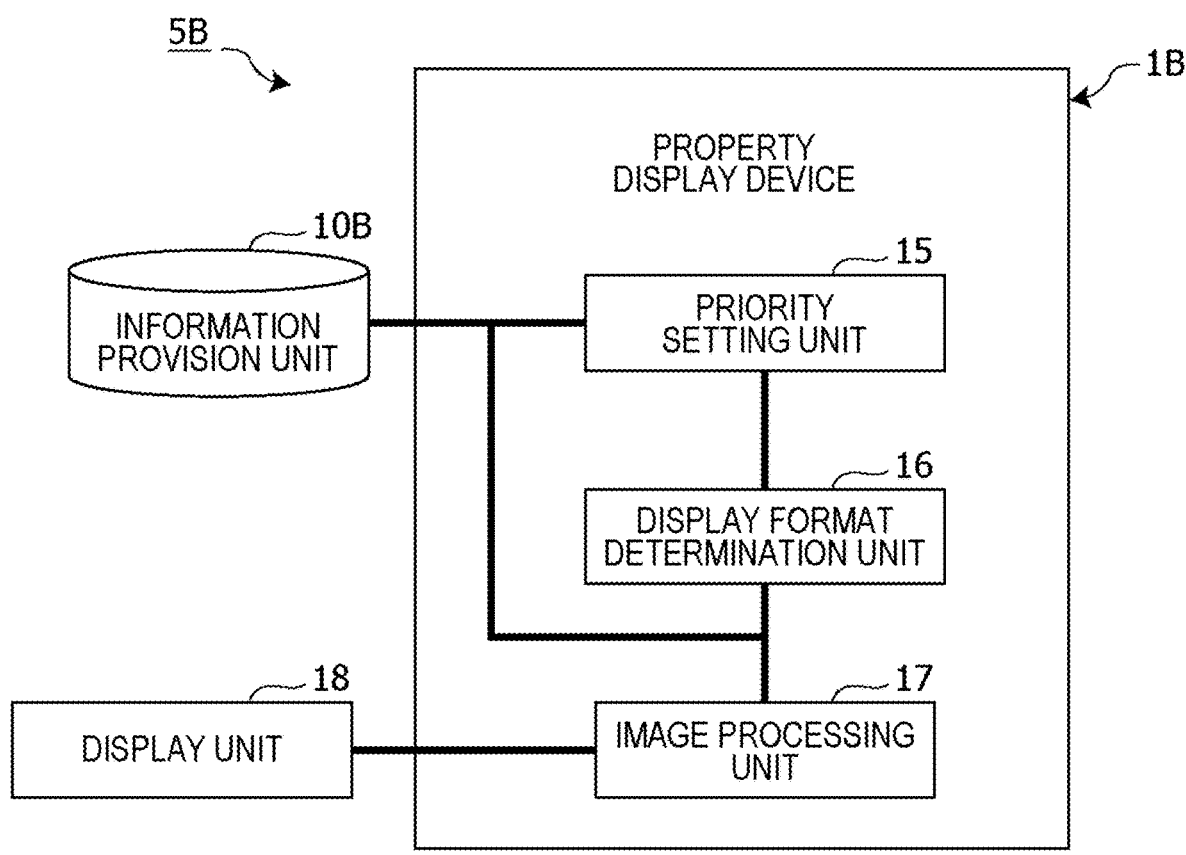
FIG. 26 is a block diagram illustrating a functional configuration of a property display system provided with a property display device according to Embodiment 3.

FIG. 26 is a block diagram illustrating a functional configuration of a property display system 5B provided with a property display device 1B according to Embodiment 3.

As illustrated in FIG. 26, the property display system 5B is provided with a property display device 1B, an information provision unit 10B, and a display unit 18. The property display device 1B is provided with a priority setting unit 15, a display format determination unit 16, and an image processing unit 17. The priority setting unit 15 in the present embodiment may be interpreted as also including the functions of the priority setting unit 15 described in Embodiment 1, except that search content provided by the information provision unit 10B is used. Similarly, the display format determination unit 16 and the image processing unit 17 in the present embodiment may be interpreted as also including the functions of the display format determination unit 16 and the image processing unit 17 described in Embodiment 1.

The property display device 1B is configured by a processor such as a CPU, volatile memory and non-volatile memory, and a program stored in the non-volatile memory, for example. The functional configuration of the property display device 1B is achieved by executing the program.

The information provision unit 10B receives search content for a compound through input operations performed by a user, for example, and provides information related to the received search content to the property display device 1B. The information provision unit 10B also provides information related to property values of the compound corresponding to the search content to the property display device 1B. The search content provided by the information provision unit 10B is inputted into the priority setting unit 15 and the image processing unit 17, and the property values are inputted into the image processing unit 17.

The priority setting unit 15 sets the priority of the search variables on the basis of the search content provided by the information provision unit 10B. A high priority is set when there is a need to closely examine the change in property values with respect to a change in the search data.

For example, from among the continuous variables, discrete variables, and category variables, the priority setting unit 15 sets the highest priority for the continuous variables which have the greatest number of search data points. In addition, the priority setting unit 15 sets the priority of the discrete variables higher than the priority of the category variables.

Also, if multiple continuous variables exist, the priority setting unit 15 sets the priority for the continuous variables such that the larger the number of search data points a continuous variable has, the higher the priority is set. Note that as an exception, the priority setting unit 15 sets the highest priority for continuous variables in which the search data has a minimum value of 0, a maximum value of 1, and the number of search data points is equal to or greater than 5. Also, if the number of search data points is the same, the priority setting unit 15 sets the priority to the same level. In the case where there are three or more continuous variables, the priority setting unit 15 likewise sets the priority on the basis of the number of search data points.

Also, if multiple discrete variables exist, the priority setting unit 15 sets the priority for the discrete variables such that the larger the number of search data points a discrete variable has, the higher the priority is set. Also, if the number of search data points is the same, the priority setting unit 15 sets the priority to the same level. In the case where there are three or more discrete variables, the priority setting unit 15 likewise sets the priority on the basis of the number of search data points.

Also, if multiple category variables exist, the priority setting unit 15 sets the priority for the category variables such that the larger the number of search data points a category variable has, the higher the priority is set. Also, if the number of search data points is the same, the priority setting unit 15 sets the priority to the same level. In the case where there are three or more category variables, the priority setting unit 15 likewise sets the priority on the basis of the number of search data points.

The priority setting unit 15 outputs the result of setting the priority as above to the display format determination unit 16.

The display format determination unit 16 determines the display format of the property of the compound on the basis of the result of setting the priority outputted from the priority setting unit 15. The display format determination unit 16 determines the display format of the property of the compound by assigning the search variables of high priority from among the search variables to the coordinate axes A1 and A2 of color maps Ma and assigning the search variables of lower priority than the search variables of high priority to the array direction axes A3 and A4 of a first array map Mb1.

The color maps Ma have a coordinate axis A1 as the horizontal axis and a coordinate axis A2 as the vertical axis. The first array map Mb1 is in a matrix form and has an array direction axis A3 as the horizontal axis and an array direction axis A4 as the vertical axis.

The display format determination unit 16 assigns the two variables with the highest and second-highest priority from among the continuous variables, discrete variables, and category variables to the two coordinate axes A1 and A2 of the color maps Ma. Moreover, the display format determination unit 16 assigns two variables of high priority from among the variables that were not assigned to the coordinate axes A1 and A2 of the color maps Ma, namely the two variables with the third- and fourth-highest priority, to the two array direction axes A3 and A4 of the first array map Mb1.

Note that if there are other search variables that were not assigned to the coordinate axes A1, A2 and the array direction axes A3, A4 from among the search variables, the display format determination unit 16 may determine that images based on the other search variables are to be displayed in another region T1 different from the color maps Ma and the first array map Mb1. For example, the display format determination unit 16 may cause the display of images based on the other search variables to be switched through the use of a scrollbar on the screen.

The display format determination unit 16 outputs the determined display format to the image processing unit 17.

The image processing unit 17 acquires the search content and property values outputted from the information provision unit 10B, and acquires the display format outputted from the display format determination unit 16. The image processing unit 17 generates an image indicating the property of the compound on the basis of the acquired search content, property values, and display format. Specifically, the image processing unit 17 generates the first array map Mb1 including the color maps Ma as a single image. That is, the image processing unit 17 visualizes information indicating the property of the compound on the basis of the acquired search content, property values, and display format. The image processing unit 17 outputs a signal including image information for the color maps Ma and the first array map Mb1 to the display unit 18.

The display unit 18 is an output unit that outputs an image indicating the property of the compound. The display unit 18 is a display device such as a liquid crystal display (LCD) panel, for example, and displays an image on the basis of the signal outputted from the image processing unit 17.

[3-2. Processing Operations by Property Display Device and the Like]

Next, processing operations by the property display device 1B and the like according to Embodiment 3 will be described.

Figure 27:
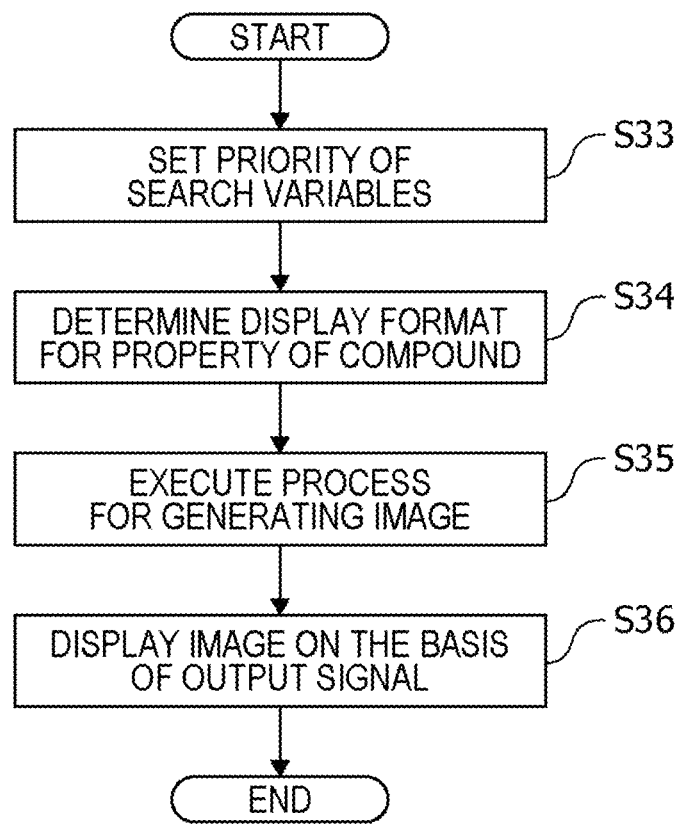
FIG. 27 is a flowchart illustrating an example of processing operations by a display unit included in the property display device and property display system according to Embodiment 3.

FIG. 27 is a flowchart illustrating an example of processing operations by the display unit 18 included in the property display device 1B and property display system 5B.

First, the priority setting unit 15 acquires the search content outputted from the information provision unit 10B and sets the priority with respect to each search variable included in the search content (step S33). For example, from among the continuous variables, discrete variables, and category variables, the priority setting unit 15 sets the highest priority for the continuous variables which have the greatest number of search data points. In addition, the priority setting unit 15 sets the priority of the discrete variables higher than the priority of the category variables. The priority setting unit 15 outputs the result of setting the priority to the display format determination unit 16.

The display format determination unit 16 determines the display format of the property of the compound on the basis of the result of setting the priority outputted from the priority setting unit 15 (step S34). Specifically, the display format determination unit 16 determines the display format of the property of the compound by assigning the search variables of high priority from among the search variables to the coordinate axes A1 and A2 of color maps Ma and assigning the search variables of lower priority than the search variables of high priority to the array direction axes A3 and A4 of a first array map Mb1. The display format determination unit 16 outputs the display format determined as above to the image processing unit 17.

The image processing unit 17 executes a process for generating an image indicating the property of the compound on the basis of the search data and property values outputted from the information provision unit 10B and the display format outputted from the display format determination unit 16 (step S35). The image processing unit 17 generates, on the basis of the acquired search data, property values, and display format, the first array map Mb1 including the color maps Ma as a single image. The image processing unit 17 outputs a signal expressing the generated image to the display unit 18.

The display unit 18 displays an image on the basis of the signal outputted from the image processing unit 17 (step S36). In the property display device 1B and the display unit 18, the display of the property of the compound is performed through the processing operations in steps S33 to S36.

[3-3. Effects and the Like]

As above, the property display device 1B according to the present embodiment includes: the priority setting unit 15 that sets the priority of search variables that determine the composition of a compound when searching for a property of the compound by changing the composition of the compound; the display format determination unit 16 that determines the display format of the property of the compound by assigning the search variables of high priority from among the search variables to the coordinate axes A1 and A2 of the color maps Ma indicating the property of the compound and assigning the search variables of lower priority than the search variables of high priority to the array direction axes A3 and A4 of the first array map Mb1 in which the color maps Ma are arranged; and the image processing unit 17 that generates at least one first array map Mb1 as a single image on the basis of the display format.

In this way, by assigning the search variables to the color maps Ma and the first array map Mb1 according to the priority of the search variables, the display format of the property of the compound can be determined appropriately. Moreover, by expressing the property of the compound with the first array map Mb1 that includes the color maps Ma, the property of the compound can be recognized with a single image. This configuration makes it possible to recognize an overall picture of a property of a compound when the composition of the compound is changed.

OTHER EMBODIMENTS

The foregoing describes a property display device and the like according to the present disclosure, but the present disclosure is not limited to the above embodiment. Embodiments obtained by applying various modifications that may occur to a person skilled in the art, embodiments formed by combining the structural elements in different embodiments, and others are also included in the scope of the present disclosure insofar as such embodiments do not depart from the gist of the present disclosure.

For example, in the above embodiment, the color maps Ma are expressed by varying shades of color in a stepwise manner, but the configuration is not limited thereto. For example, the color maps Ma may also be expressed by varying shades of color in smooth gradations, or may be expressed by differences in the density of dots. Moreover, the color maps Ma may also be expressed by differences in hues of chromatic colors, or may be expressed using achromatic colors such as white, gray, and black.

For example, the above property display device may be configured specifically by a computer system provided with a microprocessor, ROM, RAM, a hard disk drive, a display unit, a keyboard, a mouse, and the like. A property display program is stored in the RAM or the hard disk drive. The microprocessor operates in accordance with the property display program and thereby achieves the functions of the property display device. The property display program in this case is formed from a combination of instruction codes indicating commands to the computer in order to achieve a designated function.

Moreover, some or all of the structural elements forming the property display device may also be formed from a single system large-scale integration (LSI) chip. A system LSI chip is an advanced multi-function LSI chip fabricated by integrating multiple components onto a single chip, and specifically is a computer system including a microprocessor, ROM, RAM, and the like. A computer program is stored in the RAM. The microprocessor operates in accordance with the computer program and thereby achieves the functions of the system LSI chip.

Furthermore, some or all of the structural elements forming the property display device may also be formed from an IC card or a separate module that can be inserted into a computer. The IC card or module is a computer system formed from a microprocessor, ROM, RAM, and the like. The IC card or module may also include the advanced multi-function LSI chip. The microprocessor operates in accordance with the computer program and thereby achieves the functions of the IC card or module. The IC card or the module may also be tamper-resistant.

In addition, the present disclosure may also be treated as a property display method to be executed by the property display device. The property display method may be achieved by having a computer execute a property display program, or may be achieved by a digital signal containing the property display program.

Furthermore, in the present disclosure, the property display program or the digital signal may also be configured as a non-transitory computer-readable recording medium. Examples of the recording medium include a flexible disk, hard disk, CD-ROM, MO, DVD, DVD-ROM, DVD-RAM, Blu-ray® Disc (BD), or semiconductor memory. The property display program may also be configured as the digital signal recorded onto a non-transitory computer-readable recording medium.

In addition, the present disclosure may also be configured by transmitting the property display program or the digital signal over an electrical communication channel, a wired or wireless communication channel, a network such as the Internet, a data broadcast, or the like.

In addition, the present disclosure may also be a computer system provided with a microprocessor and a memory, in which the memory stores the property display program and the microprocessor operates in accordance with the property display program.

Also, the property display program or the digital signal may be implemented by another independent computer system by being recorded onto the non-transitory computer-readable recording medium and transported, or by transferring the property display program or the digital signal over the network or the like.

In addition, the property display system may be formed from a server and a terminal which is possessed by a user and which is connected to the server over a network.

The present disclosure is useful for materials development in the case of recognizing an overall picture of a property of a compound and obtaining compound having a desired property.

What is claimed is:
1. A property display device comprising:
a search content acquirer that acquires search variables that determine a composition of a compound when searching for a property of the compound by changing the composition of the compound and search data indicating values or ranges that the search variables take;
a property value acquirer that acquires property values of the compound corresponding to the search data;
a priority setter that sets a priority of the search variables;
a display format determiner that determines a display format of the property of the compound by assigning search variables of high priority from among the search variables to coordinate axes of color maps indicating the property of the compound and assigning search variables of lower priority than the search variables of high priority to array direction axes of a first array map in which the color maps are arranged; and
an image processor that generates at least one first array map as a single image on a basis of the search data, the property values, and the display format, wherein
the search variables are provided for each of one or more continuous variables, one or more discrete variables, and one or more category variables, the continuous variables have a larger number of search data points than the discrete variables and the category variables, the priority setter sets a highest priority for the continuous variables when setting the priority, the display format determiner assigns the continuous variables to the coordinate axes of the color maps, the property value acquirer keeps the search data fixed except for one of the search variables, calculates variations in the property values when the one search variable is changed for all combinations of search variables with fixed search data, and takes an average value of the variations of the property values for each of the continuous variables, the discrete variables, and the category variables, and the priority setter sets a high priority for variables having a low average value of the variations of the property values from among the continuous variables, the discrete variables, and the category variables.

2. A property display device comprising:

a search content acquirer that acquires search variables that determine a composition of a compound when searching for a property of the compound by changing the composition of the compound and search data indicating values or ranges that the search variables take;

a property value acquirer that acquires property values of the compound corresponding to the search data;

a priority setter that sets a priority of the search variables;

a display format determiner that determines a display format of the property of the compound by assigning search variables of high priority from among the search variables to coordinate axes of color maps indicating the property of the compound and assigning search variables of lower priority than the search variables of high priority to array direction axes of a first array map in which the color maps are arranged; and an image processor that generates at least one first array map as a single image on a basis of the search data, the property values, and the display format, wherein the search variables are provided for each of one or more continuous variables, one or more discrete variables, and one or more category variables, the continuous variables have a larger number of search data points than the discrete variables and the category variables, the priority setter sets a highest priority for the continuous variables when setting the priority, the display format determiner assigns the continuous variables to the coordinate axes of the color maps, the priority setter sets the priority of the category variables lower than the search variables of low priority, and the display format determiner assigns the category variables not to the coordinate axes of the color maps or to the array direction axes of the first array map, but instead to another region different from the color maps and the first array map.

3. The property display device according to claim 2, wherein if multiple category variables exist, the display format determiner assigns the category variables of high priority from among the category variables to array direction axes of a second array map in which multiple first array maps are arranged, and the image processor generates an image indicating the property of the compound on a basis of the search data, the property values, and the display format.

* * * * *